(12) United States Patent
Johnson

(10) Patent No.: US 8,362,330 B2
(45) Date of Patent: Jan. 29, 2013

(54) HIGH BIOMASS SORGHUM HYBRID CB 7520

(75) Inventor: Clinton Jay Johnson, Happy, TX (US)

(73) Assignee: Ceres, Inc., Thousand Oaks, CA (US)

( * ) Notice: Subject to any disclaimer, the term of this patent is extended or adjusted under 35 U.S.C. 154(b) by 267 days.

(21) Appl. No.: 12/942,775

(22) Filed: Nov. 9, 2010

(65) Prior Publication Data

US 2011/0113501 A1    May 12, 2011

Related U.S. Application Data

(60) Provisional application No. 61/260,067, filed on Nov. 11, 2009.

(51) Int. Cl.
*A01H 5/00* (2006.01)
*C12N 15/82* (2006.01)

(52) U.S. Cl. ......... 800/320; 800/260; 800/278; 435/410

(58) Field of Classification Search .................. None
See application file for complete search history.

(56) References Cited

U.S. PATENT DOCUMENTS

| | | | |
|---|---|---|---|
| 5,304,719 A | | 4/1994 | Segebart |
| 5,367,109 A | | 11/1994 | Segebart |
| 5,523,520 A | | 6/1996 | Hunsperger et al. |
| 5,850,009 A | | 12/1998 | Kevern |
| 2010/0064382 A1 | * | 3/2010 | Rooney et al. ................ 800/263 |

FOREIGN PATENT DOCUMENTS

| BR | 21806.000154/2012 | 7/2012 |
|---|---|---|
| WO | WO2010/011680 | 1/2010 |

OTHER PUBLICATIONS

U.S. Appl. No. 12/943,278, filed Nov. 10, 2010, Rooney, W. L.
U.S. Appl. No. 61/260,067, filed Nov. 11, 2009, Johnson, Clinton J.
Eshed, et al., 1996, Less-than-additive epistatic interactions of quantitative trait loci in tomato, Genetics 143:1807-1817.
Kraft, et al., 2000, Linkage disequilibrium and fingerprinting in sugar beet, Theor. App. Genet., 101:323-326.
Poehlman, J.M. and Sleper, D.A., Methods in Plant Breeding, Breeding Field Crops, 4th Ed. (1995), Iowa State University Press, pp. 172-174.
Goldman, et al., 1994, Molecular Markers Associated with Maize Kernel Oil Concentration in an Illinois High Protein x Illinois Low Protein Cross, Crop Sci., 34: 908-915.
US PVP Database, Application No. 201000045 of Ceres, Inc., filed Nov. 13, 2009.
Canadian PBR Database, Application No. 10-6817 of Ceres, Inc., filed Feb. 9, 2010.
US Plant Variety Protection Database, Application 201000045, Hybrid Sorghum 'CB 7520', Notice of Allowance mailed Nov. 2, 2012.

* cited by examiner

*Primary Examiner* — Li Zheng
(74) *Attorney, Agent, or Firm* — Jondle & Associates, P.C.

(57) ABSTRACT

A hybrid *sorghum*, designated CB 7520 is disclosed. The invention relates to the seeds of hybrid *sorghum* CB 7520, to the plants of hybrid *sorghum* CB 7520 and to methods for producing a *sorghum* plant by crossing the hybrid CB 7520 with itself or another *sorghum* plant that is not a plant of *sorghum* hybrid CB 7520. The invention further relates to hybrid *sorghum* seeds and plants. The invention further relates to methods for producing a *sorghum* plant containing in its genetic material one or more transgenes and to the transgenic plants produced by that method and to methods for producing other hybrid *sorghum* derived from *sorghum* hybrid CB 7520.

19 Claims, No Drawings

HIGH BIOMASS SORGHUM HYBRID CB 7520

CROSS-REFERENCE TO RELATED APPLICATIONS

This application is a non-provisional application of and claims priority to U.S. Provisional Patent Application No. 61/260,067, filed on Nov. 11, 2009, which is herein incorporated by reference in its entirety.

BACKGROUND OF THE INVENTION

The present invention relates to a new and distinctive *sorghum* hybrid, designated CB 7520. All publications cited in this application are herein incorporated by reference.

The new *sorghum* hybrid CB 7520, also known as ES5200, can be used as a biomass feedstock crop for biofuel and/or biopower applications. *Sorghum* hybrid CB 7520 may be grown for biomass, sugar, and/or forage.

As a biomass crop, *sorghum* can be of any of the many varieties which have a high biomass. Many of these varieties are photoperiod sensitive and do not flower when grown in temperate latitudes. The continuous growth of vegetative biomass uninterrupted by flowering allows these varieties to produce significantly more vegetative biomass in comparison to grain *sorghums*. These high biomass *sorghum* varieties and hybrids also comprise genetic backgrounds that have been selected for based on increased plant height, increased biomass, increased growth rate, and lack of dwarfing genes, among other traits.

As a sugar crop, *sorghum* can be of any of the many varieties which have a high sugar content. Stalks are used for producing biofuel by squeezing the juice and then fermenting the juice into a liquid biofuel, such as ethanol. Varieties of *sorghum* grown for sugar content can be open-pollinated varieties or hybrids. In addition to squeezing stalks for juice, *sorghum* biomass may be treated with chemicals or industrial processes to release simple and complex sugars which can then be used in biofuel production. Varieties of *sorghum* grown for sugar content can be characterized by high brix values or by other more refined measurements of sugar components.

As a forage crop, the genus *Sorghum* includes three principal distinct morphotypes that are used as forages: forage *sorghums*, sudangrass, and *sorghum*×sudangrass hybrids. These three morphotypes have grossly different phenotypes and different modes of principal utilization. Forage *sorghums* have very coarse stems and wide leaves, similar to corn (*Zea mays* L.), very low tillering capacity, and very slow speed of regrowth after cutting. Consequently they are used nearly exclusively as a silage crop, never for hay production and only occasionally as direct pasture. Sudangrass in comparison is very grassy, characterized by very fine stems and narrow leaf blades, profuse tiller development, and exceptionally rapid recovery after cutting or grazing. Sudangrass (*Sorghum bicolor* ssp. *sudanense* L.) is an important forage species for pasture, grazing, green chop silage, hay and seed. Sudangrass is also referred to by the scientific name *sorghum*×drummondii (Steudel) Millsp. & Chase (=*S. bicolor*×*S. arundinaceum*) (R. F. Barnes and J. B. Beard (ed.), Glossary of Crop Science Terms, Crop Science Society of America, July 1992, pg. 84). Classification and species relationships of *sorghum* and sudangrass are discussed in several reports (Harlan and deWet, 1972; Celarier, 1958). For a comprehensive review of the floral characteristics, plant culture, and methods of self-pollinating or hybridizing sudangrass, see Shertz and Dalton, *Sorghum* 41:577-588, In Hybridization of Crop Plants, Fehr et al. (ed.), American Society of Agronomy Inc. (1980). *Sorghum*×sudangrass hybrids (*Sorghum bicolor*×*S. bicolor* spp. *sudanese*) which result from crossing a *sorghum* female with a sudangrass male are generally intermediate in character expression between *sorghum* and sudangrass. *Sorghum*×sudangrass hybrids are also commonly referred to as *sorghum*-sudangrass hybrids, *sorghum*/sudangrass, and SUDAX. Adding somewhat to the confusion of the nomenclature, those skilled in the art sometimes refer to *sorghum*×sudangrass hybrids as "sudangrass hybrids". See, e.g., Miller and Stroup, 2003.

As a grain crop, *Sorghum bicolor* (L) Moench, is the fifth most important cereal after rice, wheat, maize, and barley. It constitutes the main food grain for over 750 million people who live in the semi-arid tropics of Africa, Asia, and Latin America. The largest group of producers are small-scale subsistence farmers with minimal access to production inputs such as fertiliser(s), pesticides, improved seeds (hybrids or varieties), good soil and water and improved credit facilities for their purchase.

There are many types of *sorghum* ranging in seed colour from white through red to brown. Traditional types are open-pollinated from which rural farmers retain seed for planting in the next season. Grain yields tend to be lower than the modern hybrids which are slowly being introduced. Commercial production of hybrid seed is a problem in many developing countries, and some rural farmers do not appreciate that harvested hybrid grain cannot be retained for planting the next season. Therefore they find *sorghum* production from hybrid seed expensive, even though the grain yields are higher than the land races. Resource-poor farmers prefer varieties incorporating the characteristics of resistance to insects, disease, drought, birds, and with acceptable yields of both grain for human consumption and fodder for livestock feed.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, higher biomass yield, higher sugar yield, improved composition traits, improved conversion traits, resistance to diseases and insects, better stems and roots, tolerance to low temperatures, and better agronomic characteristics on grain quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection, or a combination of these methods.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection. Inbred *sorghum* lines may be field tested in target area(s) for seed production for three or more years.

These processes, which lead to the final step of marketing and distribution of a *sorghum* hybrid, usually take from 8 to 12 years from the time the first cross is made and may rely on the development of improved breeding lines as precursors. Therefore, development of new cultivars and hybrids is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of *sorghum* plant breeding is to develop new, unique and superior *sorghum* lines and hybrids. The breeder initially selects and crosses two or more parental lines, followed by self-pollination and selection, producing many new genetic combinations. The breeder can theoretically generate billions of different genetic combinations via crossing, selfing, and mutations. The breeder has no direct control at the cellular level. Therefore, two breeders will never develop the same line, or even very similar lines, having the same *sorghum* traits.

Each year, the plant breeder selects the germplasm to advance to the next generation. This germplasm is grown under unique and different geographical, climatic and soil conditions, and further selections are then made, during and at the end of the growing season. The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large amounts of research monies to develop superior new *sorghum* cultivars.

The development of new *sorghum* lines requires the development and selection of *sorghum* lines, the crossing of these lines and selection of superior hybrid crosses. The hybrid seed is produced by manual crosses between selected male-fertile parents or by using male sterility systems. Additional data on parental lines, as well as the phenotype of the hybrid, influence the breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents which possess favorable, complementary traits are crossed to produce an $F_1$. An $F_2$ population is produced by selfing one or several $F_1$'s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

*Sorghum* inbred lines are typically developed by first crossing two parent plants which may or may not be inbred. The parents may have traits which the breeder desires to combine. Typically, a few plants are chosen from the resulting segregating F2 population, and these plants are self pollinated for several generations in combination with selecting for increased uniformity and/or increased homozygosity. The resulting new inbred lines can then be tested with other inbred lines to determine combining ability and suitability as parents for hybrids. Utilizing male sterile parental lines, *sorghum* hybrids may be made that have two (single hybrid) or three (double hybrid) parents.

Descriptions of other breeding methods that are commonly used for different traits and crops can be found in one of several reference books (e.g., Allard, 1960; Simmonds, 1979; Sneep, et. al, 1979; Fehr, 1987).

Proper testing should detect any major faults and establish the level of superiority or improvement over current lines and hybrids. In addition to showing superior performance, there must be a demand for a new line and hybrid that is compatible with industry standards or which creates a new market. The introduction of a new line or hybrid will incur additional costs to the seed producer, the grower, processor and consumer; for special advertising and marketing, altered seed and commercial production practices, and new product utilization. The testing preceding release of a new line or hybrid should take into consideration research and development costs as well as technical superiority of the final cultivar.

Sorghum, Sorghum bicolor (L.) Moench, is an important and valuable crop. Thus, a continuing goal of plant breeders is to develop stable, high yielding sorghum lines and hybrids that are agronomically sound. The reasons for this goal are obviously to maximize the amount of grain, biomass, sugar, biofuel/acre, and/or biopower/acre produced on the land used and to supply food and fuel for both animals and humans. To accomplish this goal, the sorghum breeder must select and develop sorghum plants that have the traits that result in superior lines and hybrids.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary and illustrative, not limiting in scope. In various embodiments, one or more of the above described problems have been reduced or eliminated, while other embodiments are directed to other improvements.

According to the invention, there is provided a novel sorghum hybrid designated CB 7520. This invention thus relates to the seeds of sorghum hybrid CB 7520, to the plants of sorghum hybrid CB 7520, and to methods for producing a sorghum plant produced by crossing sorghum hybrid CB 7520 with itself or another sorghum plant.

Thus, any such methods using sorghum hybrid CB 7520 are part of this invention: selfing, backcrosses, hybrid production, crosses to populations, and the like. All plants produced using sorghum hybrid CB 7520 as a parent are within the scope of this invention. Advantageously, the sorghum hybrid could be used in crosses with other, different, sorghum plants to produce first generation ($F_1$) sorghum hybrid seeds and plants with superior characteristics.

In another aspect, the present invention provides for single gene converted plants of sorghum hybrid CB 7520. The single transferred gene may preferably be a dominant or recessive allele. Preferably, the single transferred gene will confer such traits as herbicide resistance, insect resistance, resistance for bacterial, fungal, or viral disease, male fertility, male sterility, enhanced nutritional quality, and industrial usage. The single gene may be a naturally occurring sorghum gene or a transgene introduced through genetic engineering techniques.

In another aspect, the present invention provides regenerable cells for use in tissue culture of sorghum hybrid CB 7520. The tissue culture will preferably be capable of regenerating plants having the physiological and morphological characteristics of the foregoing sorghum plant, and of regenerating plants having substantially the same genotype as the foregoing sorghum plant. Preferably, the regenerable cells in such tissue cultures will be embryo, protoplast, meristematic cell, callus, pollen, glume, panicle leaf, pollen, ovule, cotyledon, hypocotyl, root, root tip, pistil, anther, floret, seed, stalk and rachis. Still further, the present invention provides sorghum plants regenerated from the tissue cultures of the invention.

Grain sorghum is an important and valuable food and feed grain crop. Thus, a continuing goal of plant breeders is to develop stable high yielding sorghum hybrids that are agronomically sound. The reasons for this goal are obvious to maximize the amount of grain produced on the land used and to supply food for both animals and humans.

In addition to the exemplary aspects and embodiments described above, further aspects and embodiments will become apparent by study of the following descriptions.

DEFINITIONS

In the description and tables which follow, a number of terms are used. In order to provide a clear and consistent understanding of the specification and claims, including the scope to be given such terms, the following definitions are provided:

Allele. Allele is any of one or more alternative forms of a gene, all of which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Biomass. Biomass includes harvestable plant tissues such as leaves, stems, and reproductive structures, or all plant tissues such as leaves, stems, roots, and reproductive structures.

Cell. Cell as used herein includes a plant cell, whether isolated, in tissue culture or incorporated in a plant or plant part.

Coding region/sequence. The region within a DNA molecule (i.e., between the start and stop codons) that encodes the amino acid sequence of a protein.

Disease resistance. As used herein, the term "disease resistance" is defined as the ability of plants to restrict the activities of a specified pest, such as an insect, fungus, virus, or bacterium.

Disease tolerance. As used herein, the term "disease tolerance" is defined as the ability of plants to endure a specified pest (such as an insect, fungus, virus, or bacterium) or an adverse environmental condition and still perform and produce in spite of this disorder.

Embryo. The embryo is the small plant contained within a mature seed.

Essentially all the physiological and morphological characteristics. A plant having essentially all the physiological and morphological characteristics means a plant having the physiological and morphological characteristics of the cultivar, except for the characteristics derived from a converted gene.

Gene Converted (Conversion). Gene converted (conversion) plant refers to plants which are developed by backcrossing, genetic engineering or mutation wherein essentially all of the desired morphological and physiological characteristics of a variety are recovered in addition to the one or more traits transferred into the variety via the backcrossing technique, genetic engineering, or mutation.

Genotype. Refers to the genetic constitution of a cell or organism.

Germination. The emergence and development from the seed embryo of those essential structures of a seedling. Germination is indicative of the ability to produce a normal plant under favorable conditions.

Herbicide resistance/tolerance. As used herein, herbicide resistance also includes herbicide tolerance. Herbicide resistance/tolerance is the ability of a plant to survive and reproduce following exposure to a dose of herbicide that would be lethal to a susceptible plant.

Increased biomass. As used herein, increased biomass refers to increased plant height, increased fresh matter yield, increased dry matter yield, and/or increased tiller number.

Pest resistance. As used herein, the term "pest resistance" is defined as the ability of plants to restrict the activities of a specified pest, such as an insect or nematode.

Pest tolerance. As used herein, the term "pest tolerance" is defined as the ability of plants to endure a specified pest (such as an insect or a nematode) still perform and produce in spite of this disorder.

Plant. As used herein, the term "plant" includes reference to an immature or mature whole plant, including a plant from which seed or anthers have been removed. A seed or embryo that will produce the plant is also considered to be the plant.

Plant characteristic. A plant characteristic can be a morphological, physiological, agronomic, or genetic feature of a plant.

Plant growth. This term refers to the process by which plants increase in size and mass. The increase in the number and size of plant organs is directly associated with an increase in cell numbers and cell size, which involves cell division, growth, expansion and differentiation. Plants utilize sunlight, water, carbon dioxide and minerals in biosynthesis to provide energy and substances required for growth. Plant growth can be generally divided into vegetative and reproductive growth in the life cycle.

Plant Height. Plant height in centimeters is taken from soil surface to the tip of the extended panicle at harvest.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

DETAILED DESCRIPTION OF THE INVENTION

Hybrid *sorghum* CB 7520 is a *Sorghum bicolor* (L.) Moench, originated from a cross conducted in Maricopa, Ariz. in 2008 by crossing two public varieties, the female parent ATx2752 with the male parent BTx623 to produce an $F_1$ female parent. The $F_1$ female parent was then crossed with male parent R07007 to produce this double cross hybrid. The double cross hybrid has stability in producing CB 7520. Plants of *sorghum* hybrid CB 7520 exhibited low variance with respect to leaf width at maturity and leaf sheath length at maturity. CB 7520 seedlings show no variance with respect to anthocyanin coloration on the coleoptile.

*Sorghum* hybrid CB 7520 has the following morphologic and other characteristics (based primarily on data collected at Thousand Oaks, Calif.).

TABLE 1

VARIETY DESCRIPTION INFORMATION

| General Categories: | |
| --- | --- |
| Kind: | Sorghum |
| Male sterile cytoplasm: | A-1 |
| Use class: | Biomass |
| Plant: | |
| Coleoptile: | Green |
| Plant pigment: | Red |

TABLE 1-continued

VARIETY DESCRIPTION INFORMATION

| Stalk: | |
| --- | --- |
| Diameter: | Mid-stout |
| Number of recessive height genes plant height genotype: | 1 |
| Tillers: | Few |
| Sweetness: | Insipid |
| Degree of senescence: | Nonsenescent |
| Leaf (first leaf below flag leaf): | |
| Width (relative to class): | Moderate |
| Color: | Dark green |
| Margin: | Wavy |
| Attitude: | Horizontal |
| Ligule: | Present |
| Midrib color: | White |

This invention is also directed to methods for producing a *sorghum* plant by crossing a first parent *sorghum* plant with a second parent *sorghum* plant wherein either the first or second parent *sorghum* plant is the *sorghum* plant of *sorghum* hybrid CB 7520. Further, both first and second parent *sorghum* plants can come from *sorghum* hybrid CB 7520. Therefore, any methods using *sorghum* hybrid CB 7520 are part of this invention: selfing, backcrosses, hybrid breeding and crosses to populations. Any plants produced using *sorghum* hybrid CB 7520 as a parent are within the scope of this invention.

Still further, this invention also is directed to methods for producing a *sorghum* hybrid CB 7520-derived *sorghum* plant by crossing *sorghum* hybrid CB 7520 with a second *sorghum* plant and growing the progeny seed, and repeating the crossing and growing steps with the *sorghum* hybrid CB 7520-derived plant from 0 to 7 times. Thus, any such methods using *sorghum* hybrid CB 7520 are part of this invention: selfing, backcrosses, hybrid production, crosses to populations, and the like. All plants and plant parts produced using *sorghum* hybrid CB 7520 as a parent are within the scope of this invention, including plants derived from *sorghum* hybrid CB 7520.

It should be understood that the inbred can, through routine manipulation of cytoplasmic or other factors, be produced in a male-sterile form. Such embodiments are also contemplated within the scope of the present claims.

As used herein, the term plant includes plant cells, plant protoplasts, plant cell tissue cultures from which corn plants can be regenerated, embryo, protoplast, meristematic cell, callus, pollen, glume, panicle leaf, pollen, ovule, cotyledon, hypocotyl, root, root tip, pistil, anther, floret, seed, stalk and rachis and the like.

FURTHER EMBODIMENTS OF THE INVENTION

Transformation Techniques

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes." Over the last fifteen to twenty years, several methods for producing transgenic plants have been developed, and the present invention, in particular embodiments, also relates to transformed versions of the claimed cultivar.

Culture for expressing desired structural genes and cultured cells are known in the art. Also as known in the art, *sorghum* is transformable and regenerable such that whole plants containing and expressing desired genes under regulatory control may be obtained. General descriptions of plant expression vectors and reporter genes and transformation protocols can be found in Gruber, et al., "Vectors for Plant Transformation," in *Methods in Plant Molecular Biology and Biotechnology*, Glick and Thompson Eds., CRC Press, Inc., Boca Raton, pp. 89-119 (1993)). Moreover GUS expression vectors and GUS gene cassettes are available from Clone Tech Laboratories, Inc. (Palo Alto, Calif.), while luciferase expression vectors and luciferase gene cassettes are available from Pro Mega Corp. (Madison, Wis.). General methods of culturing plant tissues are provided for example by Miki, et al., "Procedures for Introducing Foreign DNA into Plants" in *Methods in Plant Molecular Biology and Biotechnology*, Glick and Thompson Eds., CRC Press, Inc., Boca Raton, pp. 67-88 (1993)); and by Phillips, et al., "Cell-Tissue Culture and In-Vitro Manipulation" in *Corn & Corn Improvement*, 3rd Edition, Sprague, et al., (Eds., pp. 345-387, American Society of Agronomy Inc. (1988)). Methods of introducing expression vectors into plant tissue include the direct infection or co-cultivation of plant cells with *Agrobacterium tumefaciens*, described for example by Horsch, et al., *Science*, 227:1229 (1985). Descriptions of *Agrobacterium* vector systems and methods for *Agrobacterium*-mediated gene transfer are provided by Gruber, et al., supra.

Useful methods include but are not limited to expression vectors introduced into plant tissues using a direct gene transfer method such as microprojectile-mediated delivery, DNA injection, electroporation, and the like. More preferably expression vectors are introduced into plant tissues using a microprojectile media delivery system with a biolistic device or using *Agrobacterium*-mediated transformation. Transformant plants obtained with the protoplasm of the invention are intended to be within the scope of this invention.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed *sorghum* plants, using transformation methods as described below to incorporate transgenes into the genetic material of the *sorghum* plant(s).

Expression Vectors for Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley, et al., *Proc. Natl. Acad. Sci. U.S.A.*, 80:4803 (1983). Another commonly used selectable marker gene is the hygromycin phosphotransferase gene which confers resistance to the antibiotic hygromycin. Vanden Elzen, et al., *Plant Mol. Biol.*, 5:299 (1985).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant. Hayford, et al., *Plant Physiol.*, 86:1216 (1988); Jones, et al., *Mol. Gen. Genet.*, 210:86 (1987); Svab, et al., *Plant Mol. Biol.*, 14:197 (1990); Hille, et al., *Plant Mol. Biol.*, 7:171 (1986). Other selectable marker genes confer resistance to herbicides such as glyphosate, glufosinate, or bromoxynil. Comai, et al., *Nature*, 317:741-744 (1985); Gordon-Kamm, et al., *Plant Cell*, 2:603-618 (1990); and Stalker, et al., *Science*, 242:419-423 (1988).

Selectable marker genes for plant transformation not of bacterial origin include, for example, mouse dihydrofolate reductase, plant 5-enolpyruvylshikimate-3-phosphate synthase, and plant acetolactate synthase. Eichholtz, et al., *Somatic Cell Mol. Genet.*, 13:67 (1987); Shah, et al., *Science*, 233:478 (1986); Charest, et al., *Plant Cell Rep.*, 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS, β-galactosidase, luciferase and chloramphenicol acetyltransferase. Jefferson, R. A., *Plant Mol. Biol. Rep.*, 5:387 (1987); Teeri, et al., *EMBO J.*, 8:343 (1989); Koncz, et al., *Proc. Natl. Acad. Sci. U.S.A.*, 84:131 (1987); DeBlock, et al., *EMBO J.*, 3:1681 (1984). Another approach to the identification of relatively rare transformation events has been use of a gene that encodes a dominant constitutive regulator of the *Zea mays* anthocyanin pigmentation pathway. Ludwig, et al., *Science*, 247:449 (1990).

In vivo methods for visualizing GUS activity that do not require destruction of plant tissue are available. Molecular Probes Publication 2908, IMAGENE GREEN, pp. 1-4 (1993) and Naleway, et al., *J. Cell Biol.*, 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie, et al., *Science*, 263:802 (1994). GFP and mutants of GFP may be used as screenable markers.

Expression Vectors for Transformation: Promoters

Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissue are referred to as "tissue-specific." A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

The choice of promoter regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoter regions relative to the coding sequence. Transcription of a nucleic acid can be modulated in a similar manner.

Some suitable promoter regions initiate transcription only, or predominantly, in certain cell types. Methods for identifying and characterizing regulatory regions in plant genomic DNA are known, including, for example, those described in the following references: Jordano et al., Plant Cell, 1:855-866 (1989); Bustos et al., Plant Cell, 1:839-854 (1989); Green et al., EMBO J., 7:4035-4044 (1988); Meier et al., Plant Cell, 3:309-316 (1991); and Zhang et al., Plant Physiology, 110: 1069-1079 (1996).

Examples of various classes of promoter regions are described below. Some of the promoter regions indicated below as well as additional promoter regions are described in more detail in U.S. Patent Application Ser. Nos. 60/505,689; 60/518,075; 60/544,771; 60/558,869; 60/583,691; 60/619, 181; 60/637,140; 60/757,544; 60/776,307; 10/957,569; 11/058,689; 11/172,703; 11/208,308; 11/274,890; 60/583, 609; 60/612,891; 11/097,589; 11/233,726; 11/408,791; 11/414,142; 10/950,321; 11/360,017; PCT/US05/011105; PCT/US05/23639; PCT/US05/034308; PCT/US05/034343; and PCT/US06/038236; PCT/US06/040572; and PCT/US07/62762.

For example, the sequences of promoter regions p326, YP0144, YP0190, p13879, YP0050, p32449, 21876, YP0158, YP0214, YP0380, PT0848, PT0633, YP0128, YP0275, PT0660, PT0683, PT0758, PT0613, PT0672, PT0688, PT0837, YP0092, PT0676, PT0708, YP0396, YP0007, YP0111, YP0103, YP0028, YP0121, YP0008, YP0039, YP0115, YP0119, YP0120, YP0374, YP0101, YP0102, YP0110, YP0117, YP0137, YP0285, YP0212, YP0097, YP0107, YP0088, YP0143, YP0156, PT0650, PT0695, PT0723, PT0838, PT0879, PT0740, PT0535, PT0668, PT0886, PT0585, YP0381, YP0337, PT0710, YP0356, YP0385, YP0384, YP0286, YP0377, PD1367, PT0863, PT0829, PT0665, PT0678, YP0086, YP0188, YP0263, PT0743 and YP0096 are set forth in the sequence listing of PCT/US06/040572; the sequence of promoter region PT0625 is set forth in the sequence listing of PCT/US05/034343; the sequences of promoter regions PT0623, YP0388, YP0087, YP0093, YP0108, YP0022 and YP0080 are set forth in the sequence listing of U.S. patent application Ser. No. 11/172, 703; the sequence of promoter region PR0924 is set forth in the sequence listing of PCT/US07/62762; and the sequences of promoter regions p530c10, pOsFIE2-2, pOsMEA, pOsYp102, and pOsYp285 are set forth in the sequence listing of PCT/US06/038236.

It will be appreciated that a promoter region may meet criteria for one classification based on its activity in one plant species, and yet meet criteria for a different classification based on its activity in another plant species.

Broadly Expressing Promoters

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326, YP0144, YP0190, p13879, YP0050, p32449, 21876, YP0158, YP0214, YP0380, PT0848, and PT0633 promoters. Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

Root Promoters

Root-active promoters confer transcription in root tissue, e.g., root endodermis, root epidermis, or root vascular tissues. In some embodiments, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672, PT0688, and PT0837 promoters, which drive transcription primarily in root tissue and to a lesser extent in ovules and/or seeds. Other examples of root-preferential promoters include the root-specific subdomains of the CaMV 35S promoter (Lam et al., Proc. Natl. Acad. Sci. USA, 86:7890-7894 (1989)), root cell specific promoters reported by Conkling et al., Plant Physiol., 93:1203-1211 (1990), and the tobacco RD2 promoter.

Maturing Endosperm Promoters

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin promoter (Bustos et al., Plant Cell, 1(9):839-853 (1989)), the soybean trypsin inhibitor promoter (Riggs et al., Plant Cell, 1(6):609-621 (1989)), the ACP promoter (Baerson et al., Plant Mol. Biol., 22(2):255-267 (1993)), the stearoyl-ACP desaturase promoter (Slocombe et al., Plant Physiol., 104(4):167-176 (1994)), the soybean a' subunit of β-conglycinin promoter (Chen et al., Proc. Natl. Acad. Sci. USA, 83:8560-8564 (1986)), the oleosin promoter (Hong et al., Plant Mol. Biol., 34(3):549-555 (1997)), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., Mol. Cell. Biol., 13:5829-5842 (1993)), the beta-amylase promoter, and the barley hordein promoter. Other maturing endosperm promoters include the YP0092, PT0676, and PT0708 promoters.

Ovary Tissue Promoters

Promoters that are active in ovary tissues such as the ovule wall and mesocarp can also be useful, e.g., a polygalacturonidase promoter, the banana TRX promoter, the melon actin promoter, YP0396, and PT0623. Examples of promoters that are active primarily in ovules include YP0007, YP0111, YP0092, YP0103, YP0028, YP0121, YP0008, YP0039, YP0115, YP0119, YP0120, and YP0374.

Embryo Sac/Early Endosperm Promoters

To achieve expression in embryo sac/early endosperm, regulatory regions can be used that are active in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: Arabidopsis viviparous-1 (see, GenBank No. U93215); Arabidopsis atmyc1 (see, Urao (1996) Plant Mol. Biol., 32:571-57; Conceicao (1994) Plant, 5:493-505); Arabidopsis FIE (GenBank No. AF129516); Arabidopsis MEA; Arabidopsis FIS2 (GenBank No. AF096096); and FIE 1.1 (U.S. Pat. No. 6,906,244). Other promoters that may be suitable include those derived from the following genes: maize MAC1 (see, Sheridan (1996) Genetics, 142:1009-1020); maize Cat3 (see, GenBank No. L05934; Abler (1993) Plant Mol. Biol., 22:10131-1038). Other promoters include the following Arabidopsis promoters: YP0039, YP0101, YP0102, YP0110, YP0117, YP0119, YP0137, DME, YP0285, and YP0212. Other promoters that may be useful include the following rice promoters: p530c10, pOsFIE2-2, pOsMEA, pOsYp102, and pOsYp285.

Embryo Promoters

Regulatory regions that preferentially drive transcription in zygotic cells following fertilization can provide embryo-preferential expression. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (Plant Cell Rep (2001) 20:647-654), YP0097, YP0107, YP0088, YP0143, YP0156, PT0650, PT0695, PT0723, PT0838, PT0879, and PT0740.

Photosynthetic Tissue Promoters

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (Larix laricina), the pine cab6 promoter (Yamamoto et al., Plant Cell Physiol., 35:773-778 (1994)), the Cab-1 promoter from wheat (Fejes et al., Plant Mol. Biol., 15:921-932 (1990)), the CAB-1 promoter from spinach (Lubberstedt et al., Plant Physiol., 104: 997-1006 (1994)), the cab1R promoter from rice (Luan et al., Plant Cell, 4:971-981 (1992)), the pyruvate orthophosphate dikinase (PPDK) promoter from corn (Matsuoka et al., Proc. Natl. Acad. Sci. USA, 90:9586-9590 (1993)), the tobacco Lhcb1*2 promoter (Cerdan et al., Plant Mol. Biol., 33:245-255 (1997)), the Arabidopsis thaliana SUC2 sucrose-H+ symporter promoter (Truernit et al., Planta, 196:564-570 (1995)), and thylakoid membrane protein promoters from spinach (psaD, psaF, psaE, PC, FNR, atpC, atpD, cab, rbcS). Other photosynthetic tissue promoters include PT0535, PT0668, PT0886, YP0144, YP0380 and PT0585.

Vascular Tissue Promoters

Examples of promoters that have high or preferential activity in vascular bundles include YP0087, YP0093, YP0108, YP0022, and YP0080. Other vascular tissue-preferential promoters include the glycine-rich cell wall protein GRP 1.8 promoter (Keller and Baumgartner, Plant Cell, 3(10):1051-1061 (1991)), the Commelina yellow mottle virus (CoYMV) promoter (Medberry et al., Plant Cell, 4(2):185-192 (1992)), and the rice tungro bacilliform virus (RTBV) promoter (Dai et al., Proc. Natl. Acad. Sci. USA, 101(2):687-692 (2004)).

Inducible Promoters

Inducible promoters confer transcription in response to external stimuli such as chemical agents or environmental stimuli. For example, inducible promoters can confer transcription in response to hormones such as giberellic acid or ethylene, or in response to light or drought. Examples of drought-inducible promoters include YP0380, PT0848, YP0381, YP0337, PT0633, YP0374, PT0710, YP0356, YP0385, YP0396, YP0388, YP0384, PT0688, YP0286, YP0377, PD1367, and PD0901. Examples of nitrogen-inducible promoters include PT0863, PT0829, PT0665, and PT0886. Examples of shade-inducible promoters include PR0924 and PT0678. An example of a promoter induced by salt is rd29A (Kasuga et al. (1999) Nature Biotech 17: 287-291).

Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

Stem Promoters

A stem promoter may be specific to one or more stem tissues or specific to stem and other plant parts. Stem promoters may have high or preferential activity in, for example, epidermis and cortex, vascular cambium, procambium, or xylem. Examples of stem promoters include YP0018 which is disclosed in US20060015970 and CryIA(b) and CryIA(c) (Braga et al. 2003, Journal of New Seeds 5:209-221).

Other Promoters

Other classes of promoters include, but are not limited to, shoot-preferential, callus-preferential, trichome cell-preferential, guard cell-preferential such as PT0678, tuber-preferential, parenchyma cell-preferential, and senescence-preferential promoters. Promoters designated YP0086, YP0188, YP0263, PT0758, PT0743, PT0829, YP0119, and YP0096, as described in the above-referenced patent applications, may also be useful.

Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

Signal Sequences for Targeting Proteins to Subcellular Compartments

Transport of protein produced by transgenes to a subcellular compartment such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example, Becker, et al., *Plant Mol. Biol.*, 20:49 (1992); Close, P. S., Master's Thesis, Iowa State University (1993); Knox, C., et al., *Plant Mol. Biol.*, 9:3-17 (1987); Lerner, et al., *Plant Physiol.*, 91:124-129 (1989); Fontes, et al., *Plant Cell*, 3:483-496 (1991); Matsuoka, et al., *Proc. Natl. Acad. Sci.*, 88:834 (1991); Gould, et al., *J. Cell. Biol.*, 108:1657 (1989); Creissen, et al., *Plant J.*, 2:129 (1991); Kalderon, et al., *Cell*, 39:499-509 (1984); Steifel, et al., *Plant Cell*, 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.*, 114:92-6 (1981).

According to a preferred embodiment, the transgenic plant provided for commercial production of foreign protein is sorghum. In another preferred embodiment, the biomass of interest is seed. For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see *Methods in Plant Molecular Biology and Biotechnology*, Glick and Thompson Eds., CRC Press, Inc., Boca Raton, pp. 269-284 (1993)). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR, and sequencing, all of which are conventional techniques.

Through the transformation of sorghum, the expression of genes can be altered to enhance disease resistance, insect resistance, herbicide resistance, agronomic quality and other traits. Transformation can also be used to insert DNA sequences which control or help control male-sterility. DNA sequences native to sorghum as well as non-native DNA sequences can be transformed into sorghum and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing, or gene suppression) is desirable for several aspects of genetic engineering in plants.

Many techniques for gene silencing are well-known to one of skill in the art, including, but not limited to, knock-outs (such as by insertion of a transposable element such as mu (Vicki Chandler, The Maize Handbook, ch. 118, Springer-Verlag (1994)) or other genetic elements such as a FRT, Lox, or other site specific integration site, antisense technology (see, e.g., Sheehy, et al., *PNAS USA*, 85:8805-8809 (1988); and U.S. Pat. Nos. 5,107,065; 5,453,566; and 5,759,829); co-suppression (e.g., Taylor, *Plant Cell*, 9:1245 (1997); Jorgensen, *Trends Biotech.*, 8(12):340-344 (1990); Flavell, *PNAS USA*, 91:3490-3496 (1994); Finnegan, et al., *Bio/Technology*, 12: 883-888 (1994); and Neuhuber, et al., *Mol. Gen. Genet.*, 244:230-241 (1994)); RNA interference (Napoli, et al., *Plant Cell*, 2:279-289 (1990); U.S. Pat. No. 5,034,323; Sharp, *Genes Dev.*, 13:139-141 (1999); Zamore, et al., *Cell*, 101:25-33 (2000); and Montgomery, et al., *PNAS USA*, 95:15502-15507 (1998)); virus-induced gene silencing (Burton, et al., *Plant Cell*, 12:691-705 (2000); and Baulcombe, *Curr. Op. Plant Bio.*, 2:109-113 (1999)); target-RNA-specific ribozymes (Haseloff, et al., *Nature*, 334: 585-591 (1988)); hairpin structures (Smith, et al., *Nature*, 407:319-320 (2000); WO 99/53050; and WO 98/53083); MicroRNA (Aukerman & Sakai, *Plant Cell*, 15:2730-2741 (2003)); ribozymes (Steinecke, et al., *EMBO J.*, 11:1525 (1992); and Perriman, et al., *Antisense Res. Dev.*, 3:253 (1993)); oligonucleotide mediated targeted modification (e.g., PCT Publication Nos. WO 03/076574 and WO 99/25853); Zn-finger targeted molecules (e.g., PCT Publication Nos. WO 01/52620; WO 03/048345; and WO 00/42219); and other methods or combinations of the above methods known to those of skill in the art.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant cultivar can be transformed with cloned resistance gene to engineer plants that are resistant to specific pathogen strains. See, for example, Jones, et al., *Science*, 266:789 (1994) (cloning of the tomato Cf-9 gene for resistance to *Cladosporium fulvum*); Martin, et al., *Science*, 262:1432 (1993) (tomato Pto gene for resistance to *Pseudomonas syringae* pv. *tomato* encodes a protein kinase); Mindrinos, et al., *Cell*, 78:1089 (1994) (*Arabidopsis* RSP2 gene for resistance to *Pseudomo*-

*nas syringae*); McDowell & Woffenden, *Trends Biotechnol.*, 21(4): 178-83 (2003); and Toyoda, et al., *Transgenic Res.*, 11 (6):567-82 (2002).

B. A *Bacillus thuringiensis* protein, a derivative thereof or a synthetic polypeptide modeled thereon. See, for example, Geiser, et al., *Gene*, 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995, and 31998.

C. A lectin. See, for example, the disclosure by Van Damme, et al., *Plant Molec. Biol.*, 24:25 (1994), who disclose the nucleotide sequences of several *Clivia miniata* mannose-binding lectin genes.

D. A vitamin-binding protein such as avidin. See, PCT Appl. No. US 93/06487. The application teaches the use of avidin and avidin homologues as larvicides against insect pests.

E. An enzyme inhibitor, for example, a protease or proteinase inhibitor or an amylase inhibitor. See, for example, Abe, et al., *J. Biol. Chem.*, 262:16793 (1987) (nucleotide sequence of *sorghum* cysteine proteinase inhibitor); Huub, et al., *Plant Molec. Biol.*, 21:985 (1993) (nucleotide sequence of cDNA encoding tobacco proteinase inhibitor I); Sumitani, et al., *Biosci. Biotech. Biochem.*, 57:1243 (1993) (nucleotide sequence of *Streptomyces nitrosporeus* α-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock, et al., *Nature*, 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.*, 269:9 (1994) (expression cloning yields DNA coding for insect diuretic hormone receptor), and Pratt, et al., *Biochem. Biophys. Res. Comm.*, 163:1243 (1989) (an allostatin is identified in *Diploptera puntata*). See also, U.S. Pat. No. 5,266,317 to Tomalski, et al., who disclose genes encoding insect-specific, paralytic neurotoxins.

H. An insect-specific venom produced in nature by a snake, a wasp, etc. For example, see Pang, et al., *Gene*, 116:165 (1992), for disclosure of heterologous expression in plants of a gene coding for a scorpion insectotoxic peptide.

I. An enzyme responsible for a hyper-accumulation of a monoterpene, a sesquiterpene, a steroid, a hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See, PCT Publication No. WO 93/02197 in the name of Scott, et al., which discloses the nucleotide sequence of a callase gene. DNA molecules which contain chitinase-encoding sequences can be obtained, for example, from the ATCC under Accession Nos. 39637 and 67152. See also, Kramer, et al., Insect *Biochem. Molec. Biol.*, 23:691 (1993), who teach the nucleotide sequence of a cDNA encoding tobacco hornworm chitinase, and Kawalleck, et al., *Plant Molec. Biol.*, 21:673 (1993), who provide the nucleotide sequence of the parsley ubi4-2 polyubiquitin gene.

K. A molecule that stimulates signal transduction. For example, see the disclosure by Botella, et al., *Plant Molec. Biol.*, 24:757 (1994), of nucleotide sequences for mung bean calmodulin cDNA clones, and Griess, et al., *Plant Physiol.*, 104:1467 (1994), who provide the nucleotide sequence of a maize calmodulin cDNA clone.

L. A hydrophobic moment peptide. See, PCT Publication No. WO 95/16776 (disclosure of peptide derivatives of Tachyplesin which inhibit fungal plant pathogens) and PCT Publication No. WO 95/18855 (teaches synthetic antimicrobial peptides that confer disease resistance), the respective contents of which are hereby incorporated by reference.

M. A membrane permease, a channel former or a channel blocker. For example, see the disclosure of Jaynes, et al., *Plant Sci*, 89:43 (1993), of heterologous expression of a cecropin-β, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., *Ann. Rev. Phytopathol.*, 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor, et al., Abstract #497, Seventh International Symposium on Molecular Plant-Microbe Interactions (Edinburgh, Scotland (1994)) (enzymatic inactivation in transgenic tobacco via production of single-chain antibody fragments).

P. A virus-specific antibody. See, for example, Tavladoraki, et al., *Nature*, 366:469 (1993), who show that transgenic plants expressing recombinant antibody genes are protected from virus attack.

Q. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See, Lamb, et al., *Bio/Technology*, 10:1436 (1992). The cloning and characterization of a gene which encodes a bean endopolygalacturonase-inhibiting protein is described by Toubart, et al., *Plant J.*, 2:367 (1992).

R. A developmental-arrestive protein produced in nature by a plant. For example, Logemann, et al., *Bio/Technology*, 10:305 (1992), have shown that transgenic plants expressing the barley ribosome-inactivating gene have an increased resistance to fungal disease.

S. Genes involved in the Systemic Acquired Resistance (SAR) Response and/or the pathogenesis-related genes. Briggs, S., *Current Biology*, 5(2) (1995); Pieterse & Van Loon, *Curr. Opin. Plant Bio.*, 7(4):456-64 (2004) and Somssich, *Cell*, 113(7):815-6 (2003).

T. Antifungal genes. See, Cornelissen and Melchers, *Plant Physiol.*, 101:709-712 (1993); Parijs, et al., *Planta*, 183:258-264 (1991) and Bushnell, et al., *Can. J. of Plant Path.*, 20(2): 137-149 (1998). See also, U.S. Pat. No. 6,875,907.

U. Detoxification genes, such as for fumonisin, beauvericin, moniliformin, and zearalenone, and their structurally related derivatives. For example, see U.S. Pat. No. 5,792,931.

V. Cystatin and cysteine proteinase inhibitors. See U.S. Pat. No. 7,205,453.

W. Defensin genes. See PCT Publication No. WO 03/000863 and U.S. Pat. No. 6,911,577.

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee, et al., *EMBO J.,* 7:1241 (1988) and Miki, et al., *Theor. Appl. Genet.,* 80:449 (1990), respectively.

B. Glyphosate (resistance conferred by mutant 5-enolpyruvlshikimate-3-phosphate synthase (EPSP) and aroA genes, respectively) and other phosphono compounds such as glufosinate (phosphinothricin acetyl transferase (PAT) and *Streptomyces hygroscopicus* PAT, bar, genes), and pyridinoxy or phenoxy propionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC Accession No. 39256, and the nucleotide sequence of the mutant gene is disclosed in U.S. Pat. No. 4,769,061 to Comai. European Pat. Appl. No. 0 333 033 to Kumada, et al. and U.S. Pat. No. 4,975,374 to Goodman, et al., disclose nucleotide sequences of glutamine synthetase genes which confer resistance to herbicides such as L-phosphinothricin. The nucleotide sequence of a PAT gene is provided in European Pat. Appl. No. 0 242 246 to Leemans, et al. DeGreef, et al., *Bio/Technology,* 7:61 (1989), describe the production of transgenic plants that express chimeric bar genes coding for PAT activity. Exemplary of genes conferring resistance to phenoxy propionic acids and cyclohexones, such as sethoxydim and haloxyfop are the Accl-S1, Accl-S2, and Accl-S3 genes described by Marshall, et al., *Theor. Appl. Genet.,* 83:435 (1992).

C. An herbicide that inhibits photosynthesis, such as a triazine (psbA and gs+genes) or a benzonitrile (nitrilase gene). Przibilla, et al., *Plant Cell,* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes, et al., *Biochem. J.,* 285:173 (1992).

3. Genes that Confer or Contribute to a Value-Added Trait, Such as:

A. Modified lignin content, for example, by introducing or transforming a plant with genes that alter lignin content. See, Li, X., et al., *Plant J.* (2008) 54(4): 569-581 and Saballos, A., et al., *Genetics* (2009) 181(2): 783-795.

B. Modified plant height, for example, by introducing or transforming a plant with genes that alter plant height (Dw3 and dw3). See, Brown, P. J., et al., *Genetics.* (2008) 180(1) 629-637.

C. Modified profused wax and cuticular features, for example, by introducing or transforming plants with genes that alter the cuticle/wax pathway for improvement of abiotic stress tolerance. See, Burrow, G. B., et al., *Theor. Appl. Genet.* (2009) 118(3): 423-431 and McIntyyre, C. L., et al., *Genome* (2008) 51(7): 524-533.

D. Modified diurnal oscillation, for example, by introducing or transforming a plant with an antisense gene of starch branching enzyme (SBE). See, Mutisya, J., et al., J. Plant Physiol. (2009) 166(4): 428-434.

E. Modified fatty acid metabolism, for example, by transforming a plant with an antisense gene of stearyl-ACP desaturase to increase stearic acid content of the plant. See, Knultzon, et al., *Proc. Natl. Acad. Sci. U.S.A.,* 89:2624 (1992).

F. Decreased phytate content. 1) Introduction of a phytase-encoding gene would enhance breakdown of phytate, adding more free phosphate to the transformed plant. For example, see, Van Hartingsveldt, et al., *Gene,* 127:87 (1993), for a disclosure of the nucleotide sequence of an *Aspergillus niger* phytase gene; 2) A gene could be introduced that reduced phytate content. In maize, this, for example, could be accomplished by cloning and then reintroducing DNA associated with the single allele which is responsible for maize mutants characterized by low levels of phytic acid. See, Raboy, et al., *Maydica,* 35:383 (1990).

G. Modified cell wall composition effected, for example, by transforming plants with a gene coding for an enzyme that alters the cell wall components, such as but not limited to lignin, cellulose, xylan, hemicellulose, and saccharides. See, WO2008/069878 and US 2009-0070899 A1, for examples of genes that can be used to alter cell wall composition.

4. Male Sterility:

Genes that Control Male Sterility

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432,068, describes a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on," the promoter, which in turn allows the gene that confers male fertility to be transcribed.

A. A dominant nuclear gene, Ms(tc) controlling male sterility. See, Elkonin, L. A., *Theor. Appl. Genet.* (2005) 111(7): 1377-1384.

B. A tapetum-specific gene, RTS, a *sorghum* anther-specific gene is required for male fertility and its promoter sequence directs tissue-specific gene expression in different plant species. Luo, Hong, et. al., *Plant Molecular Biology.,* 62(3): 397-408(12) (2006). Introduction of a deacetylase gene under the control of a tapetum-specific promoter and with the application of the chemical N-Ac-PPT. See International Publication No. WO 01/29237.

C. Introduction of various stamen-specific promoters. Anther-specific promoters which are of particular utility in the production of transgenic male-sterile monocots and plants for restoring their fertility. See, U.S. Pat. No. 5,639,948. See also, International Publication Nos. WO 92/13956 and WO 92/13957.

D. Introduction of the barnase and the barstar genes. See, Paul, et al., *Plant Mol. Biol.,* 19:611-622 (1992).

Alteration of Male Sterility Systems

For additional examples of nuclear male and female sterility systems and genes, see also, U.S. Pat. Nos. 5,859,341, 6,297,426, 5,478,369, 5,824,524, 5,850,014, and 6,265,640. See also, Hanson, Maureen R., et. al., "Interactions of Mitochondrial and Nuclear Genes That Affect Male Gametophyte Development," *Plant Cell.,* 16:S154-S169 (2004), all of which are hereby incorporated by reference.

A. Modification of RNA editing within mitochondrial open reading frames. See, Pring, D. R., et al, Curr. Genet. (1998) 33(6): 429-436; Pring, D. R., et al., J. Hered. (1999) 90(3): 386-393; Pring, D. R., et al., Curr. Genet. (2001) 39(5-6): 371-376; and Hedgcoth, C., et al., Curr. Genet. (2002) 41(5): 357-365.

B. Cytoplasmic male sterility (CMS) from mutations at atp6 codons. See, Kempken, F., *FEBS. Lett.* (1998): 441(2): 159-160.

C. Inducing male sterility through heat shock. See, Wang, L., *Yi Chuan Xue Bao*. (2000) 27(9): 834-838.

D. Inducing male sterility through treatment of streptomycin on *sorghum* callus cultures. See, Elkonin, L. A., et al., *Genetica* (2008) 44(5): 663-673.

5. Genes that Create a Site for Site Specific DNA Integration:

This includes the introduction of FRT sites that may be used in the FLP/FRT system and/or Lox sites that may be used in the Cre/Loxp system. For example, see, Lyznik, et al., Site-Specific Recombination for Genetic Engineering in Plants, *Plant Cell Rep,* 21:925-932 (2003) and International Publication No. WO 99/25821, which are hereby incorporated by reference. Other systems that may be used include the Gin recombinase of phage Mu (Maeser, et al. (1991); Vicki Chandler, The Maize Handbook, ch. 118, Springer-Verlag (1994), the Pin recombinase of *E. coli* (Enomoto, et al. (1983)), and the R/RS system of the pSR1 plasmid (Araki, et al. (1992)).

6. Genes that Affect Abiotic Stress Resistance:

Genes that affect abiotic stress resistance (including, but not limited to, flowering, panicle/glume and seed development, enhancement of nitrogen utilization efficiency, altered nitrogen responsiveness, drought resistance or tolerance, cold resistance or tolerance, and salt resistance or tolerance) and increased yield under stress.

A. Modified drought stress tolerance, for example, by introducing or transforming a plant with genes conferring drought stress tolerance. See, Srinivas, G., et al., *Theor. Appl. Genet.* (2009) February; 118(4): 703-717.

B. Modified salt tolerance, for example, by introducing or transforming plants with genes that confer tolerance to salt. See, Li, Y., *Pak. J. Biol. Sci.* (2008) May; 11(9): 1268-1272.

C. Modified cold tolerance, for example by introducing or transforming plants with genes that confer cold tolerance. See, Knoll, J., et al., *Theor. Appl. Genet.* (2008) 116(4): 577-587 and Knoll, J., et al., *Theor. Appl. Genet.* (2008) 116(4): 541-543.

For example, see: International Publication No. WO 00/73475 where water use efficiency is altered through alteration of malate; U.S. Pat. Nos. 5,892,009, 5,965,705, 5,929,305, 5,891,859, 6,417,428, 6,664,446, 6,717,034, and 6,801,104, and International Publication Nos. WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; U.S. Publication No. 2004/0148654 and International Publication No. WO 01/36596 where abscisic acid is altered in plants resulting in improved plant phenotype such as increased yield and/or increased tolerance to abiotic stress; International Publication Nos. WO 2000/006341 and WO 04/090143, U.S. Publication No. 2004/0237147, and U.S. Pat. No. 6,992,237, where cytokinin expression is modified resulting in plants with increased stress tolerance, such as drought tolerance and/or increased yield. Also see, International Publication Nos. WO 02/02776, WO 2003/052063, WO 01/64898, JP 2002281975, and U.S. Pat. Nos. 6,084,153, 6,177,275, and 6,107,547 (enhancement of nitrogen utilization and altered nitrogen responsiveness). For ethylene alteration, see, U.S. Publication Nos. 2004/0128719 and 2003/0166197 and International Publication No. WO 2000/32761. For plant transcription factors or transcriptional regulators of abiotic stress, see, e.g., U.S. Publication Nos. 2004/0098764 and 2004/0078852.

Other genes and transcription factors that affect plant growth and agronomic traits such as yield, flowering, plant growth, and/or plant structure, can be introduced or introgressed into plants, see, e.g., International Publication Nos. WO 97/49811 (LHY), WO 98/56918 (ESD4), WO 97/10339, WO 96/14414 (CON), WO 96/38560, WO 01/21822 (VRN1), WO 00/44918 (VRN2), WO 99/49064 (GI), WO 00/46358 (FRI), WO 97/29123, WO 99/09174 (D8 and Rht), and U.S. Pat. Nos. 6,573,430 (TFL), 6,713,663 (FT), 6,794,560, 6,307,126 (GAI), and International Publication Nos. WO 2004/076638 and WO 2004/031349 (transcription factors).

Examples of exogenous nucleic acid sequences that can be used in the methods described herein include, but are not limited to, sequences encoding genes or fragments thereof that modulate cold tolerance, frost tolerance, heat tolerance, drought tolerance, water used efficiency, nitrogen use efficiency, pest resistance, herbicide resistance, biomass, chemical composition, plant architecture, biopower conversion properties, and/or biofuel conversion properties. In particular, exemplary sequences are described in the following applications which are incorporated herein by reference in their entirety: US20080131581, US20080072340, US20070277269, US20070214517, US 20070192907, US 20070174936, US 20070101460, US 20070094750, US20070083953, US 20070061914, US20070039067, US20070006346, US20070006345, US20060294622, US20060195943, US20060168696, US20060150285, US20060143729, US20060134786, US20060112454, US20060057724, US20060010518, US20050229270, US20050223434, and US20030217388.

Methods for *Sorghum* Transformation

Numerous methods for plant transformation have been developed, including biological and physical plant transformation protocols. See, for example, Miki, et al., "Procedures for Introducing Foreign DNA into Plants," in *Methods in Plant Molecular Biology and Biotechnology,* Glick and Thompson Eds., CRC Press, Inc., Boca Raton, pp. 67-88 (1993)). In addition, expression vectors and in vitro culture methods for plant cell or tissue transformation and regeneration of plants are available. See, for example, Gruber, et al., "Vectors for Plant Transformation," in *Methods in Plant Molecular Biology and Biotechnology,* Glick and Thompson Eds., CRC Press, Inc., Boca Raton, pp. 89-119 (1993).

A. *Agrobacterium*-mediated Transformation—One method for introducing an expression vector into plants is based on the natural transformation system of *Agrobacterium*. See, for example, Horsch, et al., *Science,* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.,* 10:1 (1991). Descriptions of *Agrobacterium* vector systems and methods for *Agrobacterium*-mediated gene transfer are provided by Gruber, et al., supra, Miki, et al., supra; Moloney, et al., *Plant Cell Reports,* 8:238 (1989); *Agrobacterium*-mediated transformation of *sorghum* is provided by Zhao, Z. Y., et al., *Plant Mol. Biol.* (2000) 44(6): 789-798 and Gurel, et al., *Plant Cell Rep.* (2009) 28(3): 429-4244. See also, U.S. Pat. No. 5,591,616, issued Jan. 7, 1997.

B. Direct Gene Transfer—Despite the fact the host range for *Agrobacterium*-mediated transformation is broad, some major cereal crop species and gymnosperms have generally been recalcitrant to this mode of gene transfer, even though some success has recently been achieved in *sorghum* and corn. Hiei, et al., *The Plant Journal*, 6:271-282 (1994) and U.S. Pat. No. 5,591,616, issued Jan. 7, 1997. Several methods of plant transformation, collectively referred to as direct gene transfer, have been developed as an alternative to *Agrobacterium*-mediated transformation.

A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. See, Casas, M., et al., Proc. Natl. Acad. Sci. U.S.A. (1993) 90(23): 11212-11216, for transformation of *sorghum* plants via microprojectile bombardment; Sanford, et al., *Part. Sci. Technol.*, 5:27 (1987); Sanford, J. C., *Trends Biotech.*, 6:299 (1988); Klein, et al., *Bio/Technology*, 6:559-563 (1988); Sanford, J. C., *Physiol Plant*, 7:206 (1990); Klein, et al., *Biotechnology*, 10:268 (1992). In corn, several target tissues can be bombarded with DNA-coated microprojectiles in order to produce transgenic plants, including, for example, callus (Type I or Type II), immature embryos, and meristematic tissue.

Another method for physical delivery of DNA to plants is sonication of target cells. Zhang, et al., *Bio/Technology*, 9:996 (1991). Additionally, liposome and spheroplast fusion have been used to introduce expression vectors into plants. Deshayes, et al., *EMBO J.*, 4:2731 (1985); Christou, et al., *Proc Natl. Acad. Sci. U.S.A.*, 84:3962 (1987). Direct uptake of DNA into protoplasts using $CaCl_2$ precipitation, polyvinyl alcohol or poly-L-ornithine has also been reported. Hain, et al., *Mol. Gen. Genet.*, 199:161 (1985) and Draper, et al., *Plant Cell Physiol.*, 23:451 (1982). Electroporation of protoplasts and whole cells and tissues have also been described. Donn, et al., In Abstracts of VIIth International Congress on Plant Cell and Tissue Culture IAPTC, A2-38, p. 53 (1990); D'Halluin, et al., *Plant Cell*, 4:1495-1505 (1992); and Spencer, et al., *Plant Mol. Biol.*, 24:51-61 (1994).

Following transformation of *sorghum* target tissues, expression of the above-described selectable marker genes allows for preferential selection of transformed cells, tissues, and/or plants using regeneration and selection methods now well known in the art.

Genetic Marker Profile Through SSR and First Generation Progeny

In addition to phenotypic observations, a plant can also be identified by its genotype. The genotype of a plant can be characterized through a genetic marker profile which can identify plants of the same variety or a related variety or be used to determine or validate a pedigree. Genetic marker profiles can be obtained by techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), which are also referred to as Microsatellites, and Single Nucleotide Polymorphisms (SNPs). For example, see, Yonemaru, J., et al., "Development of genome-wide simple sequence repeat markers using whole-genome shotgun sequences of *sorghum* (*Sorghum bicolor* (L.) Moench)" *DNA Res.* (2009) 16(3): 187-193; Duan Y., et al., "Construction of methylation linkage map based on MSAP and SSR markers in *Sorghum bicolor* (L.). IUMBMB Life (2009) 61(6): 663-669; Srinivas, G. et al., "Identification of quantitative trait loci for agronomically important traits and their association with genic-microsatellite markers in *sorghum*" *Theor. App. Genet.* (2009) 118(8): 1439-1454; Mace, E. S., et al., "A consensus genetic map of *sorghum* that integrates multiple component maps and high-throughput Diversity Array Technology (DArT) markers" *BMC Plant Biol.* (2009) 9:13; Cregan et. al, "An Integrated Genetic Linkage Map of the Soybean Genome," *Crop Science*, 39:1464-1490 (1999), and Berry, et al., "Assessing Probability of Ancestry Using Simple Sequence Repeat Profiles: Applications to Maize Inbred Lines and Soybean Varieties," *Genetics*, 165:331-342 (2003), each of which are incorporated by reference herein in their entirety.

Particular markers used for these purposes are not limited to any particular set of markers, but are envisioned to include any type of marker and marker profile which provides a means of distinguishing varieties. One method of comparison is to use only homozygous loci for *sorghum* hybrid CB 7520.

Primers and PCR protocols for assaying these and other markers are widely known in the art. In addition to being used for identification of *sorghum* hybrid CB 7520 and plant parts and plant cells of *sorghum* hybrid CB 7520, the genetic profile may be used to identify a *sorghum* plant produced through the use of *sorghum* hybrid CB 7520 or to verify a pedigree for progeny plants produced through the use of *sorghum* hybrid CB 7520. The genetic marker profile is also useful in breeding and developing backcross conversions.

The present invention comprises a *sorghum* plant characterized by molecular and physiological data obtained from the representative sample of said inbred line and or hybrid deposited with the American Type Culture Collection (ATCC). Further provided by the invention is a *sorghum* hybrid plant formed by the combination of the disclosed *sorghum* hybrid plant or plant cell with another *sorghum* plant or cell.

Means of performing genetic marker profiles using SSR polymorphisms are well-known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing hybrids or varieties it is preferable if all SSR profiles are performed in the same lab.

Primers used may be publicly available and may be found in for example in U.S. Pat. Nos. 7,232,940, 7,217,003, 7,250,556, 7,214,851, 7,195,887, and 7,192,774.

In addition, plants and plant parts substantially benefiting from the use of *sorghum* line CB 7520 in their development, such as *sorghum* line CB 7520 comprising a backcross conversion, transgene, or genetic sterility factor, may be identified by having a molecular marker profile with a high percent identity to *sorghum* hybrid CB 7520. Such a percent identity might be 95%, 96%, 97%, 98%, 99%, 99.5%, or 99.9% identical to *sorghum* hybrid CB 7520.

The SSR profile of *sorghum* hybrid CB 7520 also can be used to identify plants developed from the use of *sorghum* hybrid CB 7520, as well as cells and other plant parts thereof. Such plants may be developed using the markers identified in International Publication No. WO 00/31964, U.S. Pat. No. 6,162,967 and U.S. application Ser. No. 09/954,773. Progeny plants and plant parts produced using *sorghum* hybrid CB 7520 may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% genetic contribution from a *sorghum* hybrid or line, as measured by either percent identity or percent similarity. Unique molecular profiles may be identified with other molecular tools such as SNPs and RFLPs.

While determining the SSR genetic marker profile of the plants described supra, several unique SSR profiles may also be identified which did not appear in either parent of such *sorghum* plant. Such unique SSR profiles may arise during the breeding process from recombination or mutation. A combination of several unique alleles provides a means of identifying a plant variety, a hybrid and progeny produced from such *sorghum* plant.

Gene Conversion

When the term "*sorghum* plant" is used in the context of the present invention, this also includes any gene conversions of that line. The term gene converted plant as used herein refers to those *sorghum* plants which are developed by a plant breeding technique called backcrossing wherein essentially all of the desired morphological and physiological characteristics of a cultivar are recovered in addition to the one or more genes transferred into the cultivar via the backcrossing technique. Backcrossing methods can be used with the present invention to improve or introduce a characteristic into the line. The term backcrossing as used herein refers to the repeated crossing of a hybrid progeny back to one of the parental *sorghum* plants, the recurrent parent, for that cultivar, i.e., backcrossing 1, 2, 3, 4, 5, 6, 7, 8, 9, or more times to the recurrent parent. The parental *sorghum* plant which contributes the gene for the desired characteristic is termed the nonrecurrent or donor parent. This terminology refers to the fact that the nonrecurrent parent is used one time in the backcross protocol and therefore does not recur. The parental *sorghum* plant to which the gene or genes from the nonrecurrent parent are transferred is known as the recurrent parent as it is used for several rounds in the backcrossing protocol (Poehlman & Sleper (1994); Fehr (1987)). In a typical backcross protocol, the original cultivar of interest (recurrent parent) is crossed to a second cultivar (nonrecurrent parent) that carries the single gene or genes of interest to be transferred. The resulting progeny from this cross are then crossed again to the recurrent parent and the process is repeated until a *sorghum* plant is obtained wherein essentially all of the desired morphological and physiological characteristics of the recurrent parent are recovered in the converted plant, in addition to one or more transferred genes from the nonrecurrent parent as determined at the 5% significance level when grown in the same environmental conditions.

The selection of a suitable recurrent parent is an important step for a successful backcrossing procedure. The goal of a backcross protocol is to alter or substitute one or more traits or characteristics in the original cultivar. To accomplish this, one or more genes of the recurrent cultivar is modified or substituted with the desired gene or genes from the nonrecurrent parent, while retaining essentially all of the rest of the desired genetic, and therefore the desired physiological and morphological, constitution of the original cultivar. The choice of the particular nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic(s) being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new cultivar but that can be improved by backcrossing techniques. Single gene traits may or may not be transgenic. Examples of these traits include, but are not limited to, male sterility, waxy starch, herbicide resistance, resistance for bacterial, fungal, or viral disease, insect resistance, male fertility, enhanced nutritional quality, industrial usage, yield stability, and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196, 5,948,957, and 5,969,212, the disclosures of which are specifically hereby incorporated by reference.

Introduction of a New Trait or Locus into *Sorghum* Hybrid CB 7520

*Sorghum* hybrid CB 7520 represents a new base into which a new locus or trait may be introgressed. Direct transformation and backcrossing represent two important methods that can be used to accomplish such an introgression. The term backcross conversion and single locus conversion are used interchangeably to designate the product of a backcrossing program.

Backcross Conversions of *Sorghum* Hybrid CB 7520

A backcross conversion of *sorghum* hybrid CB 7520 occurs when DNA sequences are introduced through backcrossing (Hallauer, et al., "Corn Breeding," *Corn and Corn Improvements*, No. 18, pp. 463-481 (1988)), with *sorghum* hybrid CB 7520 utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses, and the like. Molecular marker assisted breeding or selection may be utilized to reduce the number of backcrosses necessary to achieve the backcross conversion. For example, see, Openshaw, S. J., et al., Marker-assisted Selection in Backcross Breeding, in: *Proceedings Symposium of the Analysis of Molecular Data, Crop Science Society of America*, Corvallis, Oreg. (August 1994), where it is demonstrated that a backcross conversion can be made in as few as two backcrosses.

The complexity of the backcross conversion method depends on the type of trait being transferred (single genes or closely linked genes as vs unlinked genes), the level of expression of the trait, the type of inheritance (cytoplasmic or nuclear) and the types of parents included in the cross. It is understood by those of ordinary skill in the art that for single gene traits that are relatively easy to classify, the backcross method is effective and relatively easy to manage. (See, Hallauer, et al., in *Corn and Corn Improvement*, Sprague and Dudley, Third Ed. (1998)). Desired traits that may be transferred through backcross conversion include, but are not limited to, sterility (nuclear and cytoplasmic), fertility restoration, nutritional enhancements, drought tolerance, nitrogen utilization, altered fatty acid profile, low phytate, industrial enhancements, disease resistance (bacterial, fungal or viral), insect resistance, and herbicide resistance. In addition, an introgression site itself, such as an FRT site, Lox site, or other site specific integration site, may be inserted by backcrossing and utilized for direct insertion of one or more genes of interest into a specific plant variety. In some embodiments of the invention, the number of loci that may be backcrossed into *sorghum* line CB 7520 is at least 1, 2, 3, 4, or 5, and/or no more than 6, 5, 4, 3, or 2. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of a site specific integration system allows for the integration of multiple genes at the converted loci.

Tissue Culture

Further reproduction of the variety can occur by tissue culture and regeneration. Tissue culture of various tissues of *sorghum* and regeneration of plants therefrom is well known and widely published. For example, reference may be had to Komatsuda, T., et al., Crop Sci., 31:333-337 (1991); Stephens, P. A., et al., *Theor. Appl. Genet.*, 82:633-635 (1991); Komatsuda, T., et al., *Plant Cell, Tissue and Organ Culture*, 28:103-113 (1992); Dhir, S., et al., *Plant Cell Reports*, 11:285-289 (1992); Pandey, P., et al., *Japan J. Breed.*, 42:1-5 (1992); and Shetty, K., et al., *Plant Science*, 81:245-251 (1992); as well as U.S. Pat. No. 5,024,944, issued Jun. 18, 1991 to Collins, et al., and U.S. Pat. No. 5,008,200, issued Apr. 16, 1991 to Ranch, et al. Thus, another aspect of this invention is to provide cells which upon growth and differentiation produce *sorghum* plants having the physiological and morphological characteristics of *sorghum* hybrid CB 7520.

As used herein, the term "tissue culture" indicates a composition comprising isolated cells of the same or a different type or a collection of such cells organized into parts of a plant. Exemplary types of tissue cultures are embryo, protoplast, meristematic cell, callus, pollen, glume, panicle leaf, pollen, ovule, cotyledon, hypocotyl, root, root tip, pistil, anther, floret, seed, stalk and rachis, and the like. Means for preparing and maintaining plant tissue culture are well known in the art. By way of example, a tissue culture comprising organs has been used to produce regenerated plants. U.S. Pat. Nos. 5,959,185; 5,973,234, and 5,977,445 describe certain techniques, the disclosures of which are incorporated herein by reference.

As used herein, the term "plant" includes plant cells, plant protoplasts, plant cells of tissue culture from which *sorghum* plants can be regenerated, plant calli, plant clumps, and plant cells that are intact in plants or parts of plants, such as embryo, protoplast, meristematic cell, callus, pollen, glume, panicle leaf, pollen, ovule, cotyledon, hypocotyl, root, root tip, pistil, anther, floret, seed, stalk and rachis, and the like. Thus, another aspect of this invention is to provide for cells which upon growth and differentiation produce a cultivar having essentially all of the physiological and morphological characteristics of CB 7520.

The present invention contemplates a *sorghum* plant regenerated from a tissue culture of a plant of the present invention. As is well-known in the art, tissue culture of *sorghum* can be used for the in vitro regeneration of a *sorghum* plant. Tissue culture of various tissues of *sorghum* and regeneration of plants therefrom is well-known and widely published. For example, reference may be had to Chu, Q. R., et al., "A novel basal medium for embryogenic callus induction of Southern US crosses," *Rice Biotechnology Quarterly*, 32:19-20 (1997); and Oono, K., "Broadening the Genetic Variability By Tissue Culture Methods," *Jap. J. Breed.*, 33 (Suppl. 2), 306-307, illus. 1983. Thus, another aspect of this invention is to provide cells which upon growth and differentiation produce *sorghum* plants having the physiological and morphological characteristics of hybrid CB 7520.

Duncan, et al., *Planta*, 165:322-332 (1985), reflects that 97% of the plants cultured that produced callus were capable of plant regeneration. Subsequent experiments with both cultivars and hybrids produced 91% regenerable callus that produced plants. In a further study in 1988, Songstad, et al., *Plant Cell Reports*, 7:262-265 (1988), reports several media additions that enhance regenerability of callus of two cultivars. Other published reports also indicated that "non-traditional" tissues are capable of producing somatic embryogenesis and plant regeneration. K. P. Rao, et al., *Maize Genetics Cooperation Newsletter*, 60:64-65 (1986), refers to somatic embryogenesis from glume callus cultures and B. V. Conger, et al., *Plant Cell Reports*, 6:345-347 (1987), indicates somatic embryogenesis from the tissue cultures of corn leaf segments. Thus, it is clear from the literature that the state of the art is such that these methods of obtaining plants are routinely used and have a very high rate of success.

Tissue culture of corn, for example, is described in European Patent Application Publication 160,390. Corn tissue culture procedures are also described in Green and Rhodes, "Plant Regeneration in Tissue Culture of Maize," *Maize for Biological Research*, Plant Molecular Biology Association, Charlottesville, Va., 367-372 (1982), and in Duncan, et al., "The Production of Callus Capable of Plant Regeneration from Immature Embryos of Numerous *Zea Mays* Genotypes," 165 *Planta*, 322:332 (1985). Thus, another aspect of this invention is to provide cells which upon growth and differentiation produce corn plants having the physiological and morphological characteristics of *sorghum* hybrid CB 7520.

Crossing Methods and Hybrid Production

One or more of the methods of breeding described herein can be used with the *sorghum* hybrid described herein. In some embodiments, the *sorghum* hybrid described herein can be used as a parent to produce a different *sorghum* plant. In some embodiments, the *sorghum* hybrid produced is a high biomass *sorghum*. In some embodiments, the *sorghum* hybrid described herein can be used in breeding to develop a different *sorghum* plant through further selection exclusively among plants of the hybrid or by crossing the hybrid with another *sorghum* plant and making further selections through selfed or backcrossed generations. Techniques such as haploid doubling and marker assisted selection for homozygosity can be used to accelerate the process of inbreeding.

*Sorghum* plants are bred in most cases by self pollination techniques. With the incorporation of male sterility (either genetic or cytoplasmic) cross pollination breeding techniques can also be utilized. *Sorghum* has a perfect flower with both male and female parts in the same flower located in the panicle. The flowers are usually in pairs on the panicle branches. Natural pollination occurs in *sorghum* when anthers (male flowers) open and pollen falls onto receptive stigma (female flowers). Because of the close proximity of male (anthers) and female (stigma) in the panicle, self pollination can be high. Cross pollination may occur when wind or convection currents move pollen from the anthers of one plant to receptive stigma on another plant. Cross pollination is greatly enhanced with incorporation of male sterility which renders male flowers nonviable without affecting the female flowers. Successful pollination in the case of male sterile flowers requires cross pollination.

The development of *sorghum* hybrids requires the development of homozygous inbred lines, the crossing of these lines, and the evaluation of the crosses. Pedigree breeding methods, and to a lesser extent population breeding methods, are used to develop inbred lines from breeding populations. Breeding programs combine desirable traits from two or more inbred lines into breeding pools from which new inbred lines are developed by selfing and selection of desired phenotypes. The new inbreds are crossed with other inbred lines and the hybrids from these crosses are evaluated to determine which have commercial potential.

Pedigree breeding starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically, in the pedigree method of breeding five or more generations of selfing and selection is practiced. $F_1$ to $F_2$; $F_2$ to $F_3$; $F_3$ to $F_4$; $F_4$ to $F_5$, etc.

Backcrossing can be used to improve an inbred line. Backcrossing transfers a specific desirable trait from one inbred or source to an inbred that lacks that trait. This can be accomplished for example by first crossing a superior inbred (A) (recurrent parent) to a donor inbred (non-recurrent parent), which carries the appropriate genes(s) for the trait in question. The progeny of this cross is then mated back to the superior recurrent parent (A) followed by selection in the resultant progeny for the desired trait to be transferred from the non-recurrent parent. After five or more backcross generations with selection for the desired trait, the progeny will be heterozygous for loci controlling the characteristic being transferred, but will be like the superior parent for most or almost all other genes. The last backcross generation would be selfed to give pure breeding progeny for the gene(s) being transferred.

A hybrid *sorghum* variety can be the cross of two inbred lines, each of which may have one or more desirable characteristics lacked by the other or which complement the other. The hybrid progeny of the first generation is designated F1. In the development of hybrids only the F1 hybrid plants are sought. The hybrid is more vigorous than its inbred parents. This hybrid vigor, or heterosis, can be manifested in many ways, including increased vegetative growth and increased yield.

The development of a hybrid *sorghum* variety involves five steps: (1) the formation of "restorer" and "non-restorer" germplasm pools; (2) the selection of superior plants from various "restorer" and "non-restorer" germplasm pools; (3) the selfing of the superior plants for several generations to produce a series of inbred lines, which although different from each other, each breed true and are highly uniform; (4) the conversion of inbred lines classified as non-restorers to cytoplasmic male sterile (CMS) forms, and (5) crossing the selected cytoplasmic male sterile (CMS) inbred lines with selected fertile inbred lines (restorer lines) to produce the hybrid progeny (F1).

Because *sorghum* is normally a self-pollinated plant and because both male and female flowers are in the same panicle, large numbers of hybrid seed can only be produced by using cytoplasmic male sterile (CMS) inbreds. Inbred male sterile lines are developed by converting inbred lines to CMS. This is achieved by transferring the chromosomes of the line to be sterilized into sterile cytoplasm by a series of backcrosses, using a male sterile line as a female parent and the line to be sterilized as the recurrent and pollen parent in all crosses. After conversion to male sterility the line is designated the (A) line. Lines with fertility restoring genes cannot be converted into male sterile A-lines. The original line is designated the (B) line.

Flowers of the CMS inbred are fertilized with pollen from a male fertile inbred carrying genes which restore male fertility in the hybrid (F1) plants. An important consequence of the homozygosity and homogeneity of the inbred lines is that the hybrid between any two inbreds will always be the same. Once the inbreds that give the best hybrid have been identified, the hybrid seed can be reproduced indefinitely as long as the homogeneity of the inbred parent is maintained.

Where the hybrid plants produced are for use as forage or biofuel/biopower feedstock, then it may not be necessary that the flowers of the CMS inbred are fertilized with pollen from a male fertile inbred carrying genes which restore male fertility in the hybrid (F1) plants. The flowers of the CMS inbred can fertilized with pollen from a male fertile inbred (such as a B line) chosen for combining ability with the female parent inbred line. Since seed production may not be necessary or even desirable in a high biomass *sorghum* hybrid, there may be no need to use a male inbred line that carries genes which restore male fertility.

This invention also is directed to methods for producing a *sorghum* plant by crossing a first parent *sorghum* plant with a second parent *sorghum* plant wherein the first or second parent *sorghum* plant is a *sorghum* plant of CB 7520. Further, both first and second parent *sorghum* plants can come from the *sorghum* plant CB 7520. Thus, any such methods using the *sorghum* hybrid CB 7520 are part of this invention: selfing, backcrosses, hybrid production, crosses to populations, and the like. All plants produced using *sorghum* hybrid CB 7520 as a parent are within the scope of this invention, including those derived from *sorghum* hybrid CB 7520. Advantageously, the *sorghum* hybrid could be used in crosses with other, different, *sorghum* plants to produce the first generation ($F_1$) *sorghum* hybrid seeds and plants with superior characteristics. The line of the invention can also be used for transformation where exogenous genes are introduced and expressed by the line of the invention. Genetic variants created either through traditional breeding methods using CB 7520 or through transformation of CB 7520 by any of a number of protocols known to those of skill in the art are intended to be within the scope of this invention.

The following describes breeding methods that may be used with *sorghum* hybrid CB 7520 in the development of further *sorghum* plants. One such embodiment is a method for developing a CB 7520 progeny *sorghum* plant in a *sorghum* plant breeding program comprising: obtaining the *sorghum* plant, or a part thereof, of hybrid CB 7520 utilizing said plant or plant part as a source of breeding material and selecting a CB 7520 progeny plant with molecular markers in common with CB 7520 and/or with morphological and/or physiological characteristics selected from the characteristics listed in Tables 1, 2, 4 or 6. Breeding steps that may be used in the *sorghum* plant breeding program include pedigree breeding, back crossing, mutation breeding, and recurrent selection. In conjunction with these steps, techniques such as RFLP-enhanced selection, genetic marker enhanced selection (for example SSR markers) and the making of double haploids may be utilized.

Another method involves producing a population of hybrid CB 7520 progeny *sorghum* plants, comprising crossing hybrid CB 7520 with another *sorghum* plant, thereby producing a population of *sorghum* plants, which, on average, derive 50% of their alleles from hybrid CB 7520. A plant of this population may be selected and repeatedly selfed or sibbed with a *sorghum* cultivar resulting from these successive filial generations. One embodiment of this invention is the *sorghum* hybrid produced by this method and that has obtained at least 50% of its alleles from CB 7520.

One of ordinary skill in the art of plant breeding would know how to evaluate the traits of two different plant hybrids or varieties to determine if there is no significant difference between the two traits expressed by the hybrids or varieties. For example, see, Fehr and Walt, Principles of Cultivar Development, pp. 261-286 (1987). Thus the invention includes *sorghum* hybrid CB 7520 progeny *sorghum* plants comprising a combination of at least two CB 7520 traits selected from the group consisting of those listed in Tables 1, 2, 4, and 6, or the CB 7520 combination of traits listed in the Summary of the Invention, so that said progeny *sorghum* plant is not significantly different for said traits than *sorghum* hybrid CB 7520 as determined at the 5% significance level when grown in the same environment. Using techniques described herein, molecular markers may be used to identify said progeny plant as a CB 7520 progeny plant. Mean trait values may be used to determine whether trait differences are significant, and preferably the traits are measured on plants grown under the same environmental conditions. Once such a line or hybrid is developed its value is substantial since it is important to advance the germplasm base as a whole in order to maintain or improve traits such as yield, disease resistance, pest resistance, and plant performance in extreme environmental conditions.

Progeny of *sorghum* hybrid CB 7520 may also be characterized through their filial relationship with *sorghum* hybrid CB 7520, as for example, being within a certain number of breeding crosses of *sorghum* hybrid CB 7520. A breeding cross is a cross made to introduce new genetics into the progeny, and is distinguished from a cross, such as a self or a sib cross, made to select among existing genetic alleles. The lower the number of breeding crosses in the pedigree, the closer the relationship between *sorghum* hybrid CB 7520 and its progeny and any plants derived from CB 7520. For example, progeny produced by the methods described herein may be within 1, 2, 3, 4, or 5 breeding crosses of *sorghum* hybrid CB 7520.

In some embodiments, plants of the inbred *sorghum* hybrid CB 7520 can be used as female parents to produce hybrids or as female or male parents to produce new inbred lines. In some embodiments, the *sorghum* hybrid CB 7520 can be bred with another *sorghum* plant (*Sorghum bicolor*) that also contributes to a high biomass phenotype in the resulting hybrid *sorghum* plant. In other embodiments, the *sorghum* hybrid CB 7520 can be used as a parent in breeding with exotic germplasm to make new hybrids and/or inbred lines. Examples of exotic germplasm are wild, weedy, or cultivated *sorghum* species, such as but not limited to, *Sorghum almum*, *Sorghum amplum*, *Sorghum angustum*, *Sorghum arundinaceum*, *Sorghum bicolor* (such as bicolor, guinea, caudatum, kafir, and durra), *Sorghum brachypodum*, *Sorghum bulbosum*, *Sorghum burmahicum*, *Sorghum controversum*, *Sorghum drummondii*, *Sorghum ecarinatum*, *Sorghum exstans*, *Sorghum grande*, *Sorghum halepense*, *Sorghum interjectum*, *Sorghum intrans*, *Sorghum laxiflorum*, *Sorghum leiocladum*, *Sorghum macrospermum*, *Sorghum matarankense*, *Sorghum miliaceum*, *Sorghum nigrum*, *Sorghum nitidum*, *Sorghum plumosum*, *Sorghum propinquum*, *Sorghum purpureosericeum*, *Sorghum stipoideum*, *Sorghum sudanensese*, *Sorghum timorense*, *Sorghum trichocladum*, *Sorghum versicolor*, *Sorghum virgatum*, *Sorghum vulgare*, or hybrids such as *Sorghum×almum*, or *Sorghum×drummondii*. In some embodiments, *sorghum* hybrid CB 7520 can be used as a parent in breeding with other genera, such as Saccharum.

Single Cross

A single cross hybrid is produced when two inbred lines are crossed to produce the $F_1$ progeny. Much of the hybrid vigor exhibited by $F_1$ hybrids is lost in the next generation ($F_2$). Consequently, seed from hybrid varieties is not typically used for planting stock.

Hybrid *sorghum* can be produced using wind to move the pollen. Alternating strips of the cytoplasmic male sterile inbred (female) and the male fertile inbred (male) are planted in the same field. Wind moves the pollen shed by the male inbred to receptive stigma on the female. Providing that there is sufficient isolation from sources of foreign *sorghum* pollen, the stigma of the male sterile inbred (female) will be fertilized only with pollen from the male fertile inbred (male). The resulting seed, born on the male sterile (female) plants is therefore hybrid and will form hybrid plants that have full fertility restored. In some embodiments, if the hybrid *sorghum* is used as forage or for biomass production, then it may be unnecessary to restore fertility.

Double Cross

A double cross hybrid is produced when two inbred lines are crossed to produce the $F_1$ progeny, which is then crossed with a third inbred line. This technique can be used to produce forage and high biomass *sorghum* hybrids. Such hybrids typically exhibit greater variability than single cross hybrids. This variability can be an advantage in adaptability across environments.

Top Cross

A top cross is a cross between a selection, line, clone etc., and a common pollen parent which may be a variety, inbred line, single cross, etc. The common pollen parent is called the top cross or tester parent. This type of test cross involves mating a series of individuals to a common parent to produce half-sib or full-sib families for evaluation. The test can be used to determine the general combining ability of an individual. Typically, those individuals that perform well in the testcross evaluation are advanced to trials where they are evaluated in crosses with other selected individuals. In *sorghum*, a top cross is commonly an inbred variety cross. In some embodiments, where the top cross is between inbred lines, and the resulting hybrids evaluated exhibit desirable traits, there may be no need for further testing and development, for example, where the resulting hybrids have a high biomass phenotype. In some embodiments, where the top cross is between inbred lines, and the resulting hybrids evaluated exhibit sterility, there may be no need for further testing and development.

Pedigree Breeding

Pedigree breeding starts with the crossing of two genotypes, such as *sorghum* hybrid CB 7520 and another *sorghum* plant having one or more desirable characteristics that is lacking or which complements *sorghum* hybrid CB 7520. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$; etc. After a sufficient amount of inbreeding, successive filial generations will serve to increase seed of the developed variety. Preferably, the developed variety comprises homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the nonrecurrent parent by stopping the backcrossing at an early stage and proceeding with selfing and selection. For example, a *sorghum* line may be crossed with another *sorghum* line to produce a first generation progeny plant. The first generation progeny plant may then be backcrossed to one of its parent varieties to create a $BC_1$ or $BC_2$. Progeny are selfed and selected so that the newly developed variety has many of the attributes of the recurrent parent and yet several of the desired attributes of the nonrecurrent parent. This approach leverages the value and strengths of the recurrent parent for use in new *sorghum* varieties.

Therefore, an embodiment of this invention is a method of making a backcross conversion of *sorghum* hybrid CB 7520, comprising the steps of crossing a plant of *sorghum* hybrid CB 7520 with a donor plant comprising a desired trait, selecting an $F_1$ progeny plant comprising the desired trait, and backcrossing the selected $F_1$ progeny plant to a plant of *sorghum* hybrid CB 7520. This method may further comprise the step of obtaining a molecular marker profile of *sorghum* hybrid CB 7520 and using the molecular marker profile to select for a progeny plant with the desired trait and the molecular marker profile of *sorghum* hybrid CB 7520. In one embodiment the desired trait is a mutant gene or transgene present in the donor parent.

Recurrent Selection and Mass Selection

Recurrent selection is a method used in a plant breeding program to improve a population of plants. *Sorghum* CB 7520 is suitable for use in a recurrent selection program. The method entails individual plants cross pollinating with each other to form progeny. The progeny are grown and the superior progeny selected by any number of selection methods, which include individual plant, half-sib progeny, full-sib progeny and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic cultivar. A synthetic cultivar is the resultant progeny formed by the intercrossing of several selected varieties.

Mass selection is a useful technique when used in conjunction with molecular marker enhanced selection. In mass selection seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self pollination, directed pollination could be used as part of the breeding program.

Mutation Breeding

Mutation breeding is another method of introducing new traits into *sorghum* hybrid CB 7520. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g., cobalt 60 or cesium 137), neutrons (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in "Principles of Cultivar Development," Fehr, Macmillan Publishing Company (1993). In addition, mutations created in other *sorghum* plants may be used to produce a backcross conversion of *sorghum* hybrid CB 7520 that comprises such mutation.

Breeding with Molecular Markers

Molecular markers may be used in plant breeding methods utilizing *sorghum* line CB 7520.

Isozyme Electrophoresis and RFLPs have been widely used to determine genetic composition. See, for example, Dinka, S. J., et al., "Predicting the size of the progeny mapping population required to positionally clone a gene," *Genetics.*, 176(4):2035-54 (2007); Gonzalez, C., et al., "Molecular and pathogenic characterization of new *Xanthomonas oryzae* strains from West Africa," *Mol. Plant. Microbe Interact.*, 20(5):534-546 (2007); Jin, H., et al., "Molecular and cytogenic characterization of an *Oryza officinalis—O. sativa* chromosome 4 addition line and its progenies," *Plant Mol. Biol.*, 62(4-5):769-777 (2006); Pan, G., et al., "Map-based cloning of a novel *sorghum* cytochrome P450 gene CYP81A6 that confers resistance to two different classes of herbicides," *Plant Mol. Biol.*, 61(6):933-943 (2006); Huang, W., et al., "RFLP analysis for mitochondrial genome of CMS-*sorghum*," *Journal of Genetics and Genomics.*, 33(4):330-338 (2007); and I. K. Vasil (ed.), *DNA-based markers in plants*, Kluwer Academic Press Dordrecht, the Netherlands.

SSR technology is currently the most efficient and practical marker technology; more marker loci can be routinely used and more alleles per marker locus can be found using SSRs in comparison to RFLPs. See for example, Yonemaru, Jun-ichi, et al., "Development of Genome-wide Simple Sequence Repeat Markers Using Whole-genome Shotgun Sequences of

*Sorghum* (*Sorghum bicolor* (L.) Moench) *DNA Research.* Published online April 2009 and Menz, Monica A., et al. "Genetic Diversity of Public Inbreds of *Sorghum* Determined by Mapped AFLP and SSR Markers" Crop Science. 44:1236-1244 (2004). Single Nucleotide Polymorphisms may also be used to identify the unique genetic composition of the invention and progeny varieties retaining that unique genetic composition. Various molecular marker techniques may be used in combination to enhance overall resolution.

*Sorghum* DNA molecular marker linkage maps have been rapidly constructed and widely implemented in genetic studies. See, Paterson, A. H., *Int. J. Plant Genomics* (2008) 2008: 362451; Rouline A., et al., "Whole genome surveys of rice, maize and *sorghum* reveal multiple horizontal transfers of the LTR-retrotransposon Route66 in Poaceae" *BMC Evol. Biol.* (2009) 9:58; Paterson, A. H., et al., "The *Sorghum bicolor* genome and the diversification of grasses" *Nature* (2009) 457(7229): 551-556; Sasaki, T., et al., "Plant genomics: *sorghum* in sequence" *Nature* (2009) 457(7229): 547-548.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome. See Winn, J. A., et al. (2009) "QTL mapping of a high protein digestibility trait in *Sorghum* bicolor" *Int. J. Plant Genomics,* 2009:471853, Epub. 2009 Jul. 7.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Production of Double Haploids

The production of double haploids can also be used for the development of plants with a homozygous phenotype in the breeding program. For example, a *sorghum* plant for which *sorghum* line CB 7520 is a parent can be used to produce double haploid plants. Double haploids are produced by the doubling of a set of chromosomes (1N) from a heterozygous plant to produce a completely homozygous individual. For example, see, Wan, et al., "Efficient Production of Doubled Haploid Plants Through Colchicine Treatment of Anther-Derived Maize Callus," *Theoretical and Applied Genetics,* 77:889-892 (1989), and U.S. Pat. No. 7,135,615.

Methods for obtaining haploid plants are also disclosed in Kobayashi, M., et al., *Journ. of Heredity,* 71(1):9-14 (1980), Pollacsek, M., 12(3):247-251, Agronomie, Paris (1992); Cho-Un-Haing, et al., *Journ. of Plant Biol.,* 39(3):185-188 (1996); Verdoodt, L., et al., 96(2):294-300 (February 1998); Genetic Manipulation in Plant Breeding, Proceedings International Symposium Organized by EUCARPIA, Berlin, Germany (Sep. 8-13, 1985); Thomas, W J K, et al., "Doubled haploids in breeding," in Doubled Haploid Production in Crop Plants, Maluszynski, M., et al. (Eds.), Dordrecht, The Netherland Kluwer Academic Publishers, pp. 337-349 (2003).

Descriptions of other breeding methods that are commonly used for different traits and crops can be found in one of several reference books (e.g., Allard (1960); Simmonds (1979); Sneep, et al. (1979); Fehr (1987)).

Uses of *Sorghum*

The seed of *sorghum* hybrid CB 7520, the plant produced from seed of CB 7520, a plant derived from using hybrid *sorghum* CB 7520, and various parts of the hybrid *sorghum* plant and transgenic versions of the foregoing, can be utilized for human food, livestock feed, biofuel feedstock, biopower feedstock, and as a raw material in industry.

*Sorghum* is used as livestock feed, a biofuel feedstock, a biopower feedstock, as human food, and as raw material in industry. *Sorghum* grain and plant parts are used as livestock feed. *Sorghum* grain or products therefrom can be consumed by humans and can be used in making an alcoholic beverage. *Sorghum* dry milling products include, for example, grits, meal and flour. Starch and other extracts for food use can be provided by the wet milling process. *Sorghum* starch and flour have application in the paper and textile industries. Other industrial uses include applications in adhesives, building materials and as oil-well muds. Considerable amounts of *sorghum*, both grain and plant material, have been used in industrial alcohol production.

In some embodiments, plants described herein and/or hybrids therefrom have a biomass yield and/or composition that permits efficient processing into free sugars, and subsequently ethanol, for energy production. In some embodiments, such plants provide higher yields of ethanol, butanol, dimethyl ether, cellulosic gasoline, other biofuel molecules, and/or sugar-derived co-products per kilogram of plant material, relative to control plants. By providing improved yields at an equivalent or even decreased cost of production, the plants described herein improve profitability for farmers and processors as well as decrease costs to consumers. Biomass of *sorghum* described herein can also be used in biopower applications in thermal or thermochemical conversion processes to produce energy. In some embodiments, plants described herein and/or hybrids therefrom have a biomass yield and/or composition that permits efficient processing into chopped biomass, pelleted biomass, and/or bricked biomass for biopower production.

Seeds from plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material, or a label inserted within the package, that describes the nature of the seeds therein.

TABLES

In Table 2, the coleoptile seedling anthocyanin coloration of *sorghum* hybrid CB 7520 is compared to *sorghum* hybrid ES5201. Seeds were planted on Sep. 11, 2009 in a greenhouse in Thousand Oaks, Calif. and data was collected on Sep. 22, 2009. Seedlings were at the 3-leaf stage at the time of data collection. Anthocyanin values are based on a scale from 0 to 9, where 0=no anthocyanin and 9=very strong anthocyanin color. Column 1 shows the plant number, column 2 shows the anthocyanin value for *sorghum* hybrid CB 7520 and column 3 shows the anthocyanin value for *sorghum* hybrid ES5201. Blank cells indicate that the plant died.

Table 3 shows statistical analysis using ANOVA of the data contained in Table 2 and indicates that there were significant differences (P=0.001928) in the seedling coleoptile anthocyanin coloration between *sorghum* hybrids CB 7520 and ES5201.

TABLE 2

Coleoptile Seedling Anthocyanin Coloration:
Anthocyanin values are based on a scale from
0 to 9, where 0 = no anthocyanin and
9 = very strong anthocyanin color

| Plant # | ES5200 | ES5201 |
|---|---|---|
| 1 | 0 | 0 |
| 2 | 0 | 0 |
| 3 | 0 | 1 |
| 4 | 0 | 1 |
| 5 | 0 | 0 |
| 6 | 0 | 0 |
| 7 | 0 | 0 |
| 8 | 0 | 2 |
| 9 | 0 | 0 |
| 10 | 0 | 0 |
| 11 | 0 | 1 |
| 12 | 0 | 0 |
| 13 | 0 | 1 |
| 14 | 0 | 1 |
| 15 | 0 | 0 |
| 16 | 0 | 0 |
| 17 | 0 | 2 |
| 18 | 0 | 0 |
| 19 | 0 | 0 |
| 20 | 0 | 1 |
| 21 | 0 | 0 |
| 22 | 0 | 0 |
| 23 | 0 | 1 |
| 24 | 0 | 0 |
| 25 | 0 | 0 |
| 26 | 0 | 1 |
| 27 | 0 | 0 |
| 28 | 0 | 0 |
| 29 | 0 | 0 |
| 30 |  | 0 |
| 31 |  | 0 |
| 32 |  | 0 |
| 33 |  | 0 |

In Table 4, the anthocyanin coloration of the first leaf sheath of *sorghum* hybrid CB 7520 is compared to *sorghum* hybrid ES5201. Seeds were planted on Sep. 11, 2009 in a greenhouse in Thousand Oaks, Calif. and data was collected on Sep. 22, 2009. Seedlings were at the 3-leaf stage at the time of data collection. Anthocyanin values are based on a scale from 0 to 9, where 0=no anthocyanin and 9=very strong anthocyanin color. Column 1 shows the plant number, column 2 shows the anthocyanin value for *sorghum* hybrid CB 7520 and column 3 shows the anthocyanin value for *sorghum* hybrid ES5201. Blank cells indicate that the plant died.

Table 5 shows the statistical analysis using ANOVA of the data contained in Table 4 and indicate that there were significant differences (P=0.012845) in the anthocyanin coloration of first leaf sheath between *sorghum* hybrids CB 7520 and ES5201.

TABLE 4

Anthocyanin Coloration of the First Leaf Sheath:
Anthocyanin values are based on a scale from
0 to 9, where 0 = no anthocyanin and
9 = very strong anthocyanin color

| Plant # | ES5200 | ES5201 |
|---|---|---|
| 1 | 1 | 0 |
| 2 | 0 | 1 |
| 3 | 1 | 3 |
| 4 | 0 | 0 |
| 5 | 0 | 2 |
| 6 | 0 | 0 |
| 7 | 2 | 1 |
| 8 | 1 | 2 |
| 9 | 1 | 0 |
| 10 | 0 | 2 |
| 11 | 0 | 2 |
| 12 | 1 | 0 |
| 13 | 0 | 1 |
| 14 | 0 | 1 |
| 15 | 1 | 0 |
| 16 | 0 | 0 |
| 17 | 1 | 3 |
| 18 | 0 | 0 |
| 19 | 0 | 2 |
| 20 | 1 | 2 |
| 21 | 0 | 1 |
| 22 | 0 | 2 |
| 23 | 0 | 0 |
| 24 | 2 | 0 |
| 25 | 1 | 2 |
| 26 | 0 | 0 |

TABLE 3

ANOVA: Single Factor

SUMMARY

| Groups | Count | Sum | Average | Variance |
|---|---|---|---|---|
| ES5200 | 29 | 0 | 0 | 0 |
| ES5201 | 33 | 12 | 0.363636 | 0.363636 |

ANOVA

| Source of Variation | SS | df | MS | F | P-value | F crit |
|---|---|---|---|---|---|---|
| Between Groups | 2.041056 | 1 | 2.041056 | 10.52419 | 0.001928 | 4.001194 |
| Within Groups | 11.63636 | 60 | 0.193939 |  |  |  |
| Total | 13.67742 | 61 |  |  |  |  |

TABLE 4-continued

Anthocyanin Coloration of the First Leaf Sheath:
Anthocyanin values are based on a scale from
0 to 9, where 0 = no anthocyanin and
9 = very strong anthocyanin color

| Plant # | ES5200 | ES5201 |
|---|---|---|
| 27 | 1 | 1 |
| 28 | 0 | 2 |
| 29 | 0 | 0 |
| 30 |   | 2 |
| 31 |   | 1 |
| 32 |   | 0 |
| 33 |   | 1 |

TABLE 5

ANOVA: Single Factor

SUMMARY

| Groups | Count | Sum | Average | Variance |
|---|---|---|---|---|
| ES5200 | 29 | 14 | 0.482759 | 0.401478 |
| ES5201 | 33 | 34 | 1.030303 | 0.967803 |

ANOVA

| Source of Variation | SS | df | MS | F | P-value | F crit |
|---|---|---|---|---|---|---|
| Between Groups | 4.627633 | 1 | 4.627633 | 6.577847 | 0.012845 | 4.001194 |
| Within Groups | 42.21108 | 60 | 0.703518 |  |  |  |
| Total | 46.83871 | 61 |  |  |  |  |

In Table 6, various characteristics of the plants of *sorghum* hybrid CB 7520 are compared with *sorghum* hybrid ES5201. Seeds were planted in spring 2008 in Maricopa, Ariz. and data from 10 plants of each hybrid from the center of the field was collected in September 2009. Row spacing was about 2 feet and seed spacing was about 6 inches. Row 2 shows the plant number, rows 4-7 show the number of nodes (from 6 feet from the base of the plant), the leaf width in centimeters, the leaf sheath length in centimeters for *sorghum* hybrid CB 7520, respectively, and rows 9-12 show the number of nodes (from 6 feet from the base of the plant), the leaf width in centimeters, the leaf sheath length in centimeters for *sorghum* hybrid ES5201, respectively and column 12 shows the averages for each characteristic.

Table 7 shows the statistical analysis using a T-test (assuming unequal variances) of the data contained in Table 6. The null hypotheses is that the mean differences in the number of nodes, the leaf width, the leaf sheath length and the stem diameter are equal (zero difference) between *sorghum* hybrids CB 7520 and ES5201. Thus, the analyses indicate that for the number of nodes, the spread in the means for the two hybrids would have occurred about approximately 8.3 percent of the time (P=0.083546 and within a 10% confidence level). For leaf width and leaf sheaf, the differences fall within a 95% confidence level (P=0.037571 and P=0.034058, respectively). For the stem diameter, P=0.161815, which is greater than a 10% confidence level and typically not significant.

TABLE 6

| | Plant Number | | | | | | | | | | |
|---|---|---|---|---|---|---|---|---|---|---|---|
| | 1 | 2 | 3 | 4 | 5 | 6 | 7 | 8 | 9 | 10 | AVG |
| ES5200 | | | | | | | | | | | |
| No. nodes (in 6 ft from base) | 15 | 20 | 17 | 20 | 19 | 20 | 23 | 23 | 23 | 21 | 20.1 |
| Leaf width (cm) | 9 | 10 | 8.5 | 8 | 9.5 | 9.5 | 9 | 10 | 9.5 | 8.5 | 9.15 |
| Leaf sheath length (cm) | 19 | 19.5 | 18 | 20 | 18 | 20 | 19 | 17.5 | 19 | 24 | 19.4 |
| Stem diameter, 1 ft from base (cm) | 27 | 32 | 25 | 28 | 28 | 31 | 37 | 30 | 31 | 21 | 29 |
| ES5201 | | | | | | | | | | | |
| No. nodes (in 6 ft from base) | 19 | 19 | 17 | 18 | 19 | 18 | 17 | 19 | 20 | 18 | 18.4 |
| Leaf width (cm) | 9 | 7 | 8.5 | 8 | 9 | 8 | 9.5 | 8.5 | 9 | 8 | 8.45 |
| Leaf sheath length (cm) | 20 | 23 | 20 | 22 | 21 | 21 | 20 | 23 | 19 | 21.5 | 21.05 |
| Stem diameter, 1 ft from base (cm) | 30 | 35 | 25 | 32 | 27 | 33 | 32 | 34 | 37 | 31 | 31.6 |

TABLE 7

| | ES5200 | ES5201 |
|---|---|---|
| NODES | | |
| t-Test: Two-Sample Assuming Unequal Variances | | |
| Mean | 20.1 | 18.4 |
| Variance | 6.988889 | 0.933333 |
| Observations | 10 | 10 |
| Hypothesized Mean Difference | 0 | |
| df | 11 | |
| t Stat | 1.909965 | |
| P(T <= t) one-tail | 0.041273 | |
| t Critical one-tail | 1.795884 | |
| P(T <= t) two-tail | 0.082546 | |
| t Critical two-tail | 2.200986 | |
| LEAF SHEATH LENGTH | | |
| t-Test: Two-Sample Assuming Unequal Variances | | |
| Mean | 19.4 | 21.05 |
| Variance | 3.322222 | 1.802778 |
| Observations | 10 | 10 |
| Hypothesized Mean Difference | 0 | |
| df | 17 | |
| t Stat | −2.30482 | |
| P(T <= t) one-tail | 0.017029 | |
| t Critical one-tail | 1.739606 | |
| P(T <= t) two-tail | 0.034058 | |
| t Critical two-tail | 2.109819 | |
| LEAF WIDTH | | |
| t-Test: Two-Sample Assuming Unequal Variances | | |
| Mean | 9.15 | 8.45 |
| Variance | 0.447222 | 0.525 |
| Observations | 10 | 10 |
| Hypothesized Mean Difference | 0 | |
| df | 18 | |
| t Stat | 2.244994 | |
| P(T <= t) one-tail | 0.018785 | |
| t Critical one-tail | 1.734063 | |
| P(T <= t) two-tail | 0.037571 | |
| t Critical two-tail | 2.100924 | |
| STEM DIAMETER | | |
| t-Test: Two-Sample Assuming Unequal Variances | | |
| Mean | 29 | 31.6 |
| Variance | 18.66667 | 12.93333 |
| Observations | 10 | 10 |
| Hypothesized Mean Difference | 0 | |
| df | 17 | |
| t Stat | −1.46261 | |
| P(T <= t) one-tail | 0.080908 | |
| t Critical one-tail | 1.739606 | |
| P(T <= t) two-tail | 0.161815 | |
| t Critical two-tail | 2.109819 | |

DEPOSIT INFORMATION

A deposit of the Ceres, Inc. proprietary hybrid *Sorghum* CB 7520, also known as ES5200, disclosed above and recited in the appended claims has been made with the American Type Culture Collection (ATCC), 10801 University Boulevard, Manassas, Va. 20110. The date of deposit was Sep. 24, 2010. The deposit of 2,500 seeds was taken from the same deposit maintained by Ceres, Inc. since prior to the filing date of this application. All restrictions will be removed upon granting of a patent, and the deposit is intended to meet all of the requirements of 37 C.F.R. §§1.801-1.809. The ATCC Accession Number is PTA-11366. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A seed of hybrid *sorghum* designated CB 7520, wherein a representative sample of seed of said hybrid was deposited under ATCC Accession No. PTA-11366.

2. A *sorghum* plant, or a part thereof, produced by growing the seed of claim 1.

3. A *sorghum* plant, or a part thereof, having all the physiological and morphological characteristics of hybrid CB 7520, wherein a representative sample of seed of said hybrid was deposited under ATCC Accession No. PTA-11366.

4. A tissue culture of cells produced from the plant of claim 2, wherein said cells of the tissue culture are produced from a plant part selected from the group consisting of pollen, glume, panicle, leaf, pollen, ovule, cotyledon, hypocotyl, root, root tip, pistil, anther, floret, seed, stalk, immature embryo, and rachis.

5. A *sorghum* plant regenerated from the tissue culture of claim 4, wherein the regenerated plant has all the morphological and physiological characteristics of hybrid CB 7520, wherein a representative sample of seed of said hybrid was deposited under ATCC Accession No. PTA-11366.

6. A method for producing an inbred *sorghum* seed, wherein the method comprises crossing the plant of claim 2 with a same or a different *sorghum* plant, self-pollinating for generations and harvesting the resultant *sorghum* seed.

7. A method for producing a *sorghum* plant that contains in its genetic material one or more transgenes, wherein the method comprises crossing the *sorghum* plant of claim 2 with either of another *sorghum* plant which contains a transgene or a transformed *sorghum* plant of hybrid *sorghum* CB 7520, so that the genetic material of the progeny that results from the cross contains the transgene(s) operably linked to a regulatory element.

8. A *sorghum* plant produced by the method of claim 7, wherein the plant contains in its genetic material one or more transgenes and has all of the physiological and morphological characteristics of hybrid *sorghum* CB 7520.

9. A method of producing an herbicide resistant *sorghum* plant, wherein said method comprises introducing a gene conferring herbicide resistance into the plant of claim 2, and selecting for transgenic plants that have herbicide resistance and all of the physiological and morphological characteristics of hybrid *sorghum* CB 7520.

10. An herbicide resistant *sorghum* plant produced by the method of claim 9, wherein the gene confers resistance to an herbicide selected from the group consisting of glyphosate, sulfonylurea, imidazolinone, dicamba, glufosinate, phenoxy proprionic acid, L-phosphinothricin, cyclohexone, cyclohexanedione, triazine and benzonitrile.

11. A method of producing a pest or insect resistant *sorghum* plant, wherein said method comprises introducing a gene conferring pest or insect resistance into the *sorghum* plant of claim 2, and selecting for transgenic plants that have pest or insect resistance and all of the physiological and morphological characteristics of hybrid *sorghum* CB 7520.

12. A pest or insect resistant *sorghum* plant produced by the method of claim 11.

13. The *sorghum* plant of claim 12, wherein the transgene encodes a *Bacillus thuringiensis* protein.

14. A method of producing a disease resistant *sorghum* plant, wherein said method comprises introducing a gene which confers disease resistance into the *sorghum* plant of claim 2, and selecting for transgenic plants that have disease resistance and all of the physiological and morphological characteristics of hybrid *sorghum* CB 7520.

15. A disease resistant *sorghum* plant produced by the method of claim 14.

16. A method of producing a *sorghum* plant with modified fatty acid metabolism or modified carbohydrate metabolism, wherein the method comprises introducing a gene encoding a protein selected from the group consisting of phytase, fructosyltranferase, levansucrase, α-amylase, invertase and starch branching enzyme or DNA encoding an antisense of stearyl-ACP desaturase into the *sorghum* plant of claim 2, and selecting for transgenic plants that have modified fatty acid metabolism or modified carbohydrate metabolism and all of the physiological and morphological characteristics of hybrid *sorghum* CB 7520.

17. A *sorghum* plant produced by the method of claim 16 having modified fatty acid metabolism or modified carbohydrate metabolism.

18. A method for producing a seed of a plant derived from hybrid *sorghum* CB 7520 comprising the steps of:
  a) crossing the plant of claim 2 with itself or a different *sorghum* plant; and
  b) allowing seed of a hybrid CB 7520-derived *sorghum* plant to form.

19. The method of claim 18, further comprising the steps of:
  c) selfing a plant grown from said hybrid CB 7520-derived *sorghum* seed to yield additional hybrid CB 7520-derived seed of step b);
  d) growing said additional hybrid CB 7520-derived seed to produce *sorghum* plants; and
  e) repeating the growing and crossing steps of c) and d) to generate at least a first hybrid CB 7520-derived *sorghum* plant.

* * * * *